(12) United States Patent
Brzezinski et al.

(10) Patent No.: US 8,759,033 B2
(45) Date of Patent: Jun. 24, 2014

(54) CSNR-DEFICIENT ACTINOBACTERIA FOR THE PRODUCTION OF AN ENZYME HAVING CHITOSANASE ACTIVITY

(71) Applicant: Socpra Sciences et Genie S.E.C., Sherbrooke (CA)

(72) Inventors: Ryszard Brzezinski, Sherbrooke (CA); Marie-Pierre Dubeau, Sherbrooke (CA)

(73) Assignee: Socpra Sciences et Genie S.E.C., Sherbrooke (CA)

( * ) Notice: Subject to any disclaimer, the term of this patent is extended or adjusted under 35 U.S.C. 154(b) by 0 days.

(21) Appl. No.: 13/762,984

(22) Filed: Feb. 8, 2013

(65) Prior Publication Data
US 2013/0210077 A1    Aug. 15, 2013

Related U.S. Application Data

(60) Provisional application No. 61/596,764, filed on Feb. 9, 2012.

(51) Int. Cl.
  *C12N 1/21*    (2006.01)
  *C12N 15/76*   (2006.01)

(52) U.S. Cl.
  CPC .................................... *C12N 15/76* (2013.01)
  USPC ........ 435/84; 435/252.3; 435/71.2; 435/69.1; 435/252.35; 435/101; 435/209; 435/100; 435/105; 435/99

(58) Field of Classification Search
  None
  See application file for complete search history.

(56) References Cited

U.S. PATENT DOCUMENTS

| 5,482,843 A | 1/1996 | Brzezinski |
| 2011/0143394 A1 | 6/2011 | Rigali et al. |
| 2012/0114797 A1* | 5/2012 | Perkins et al. .................. 426/48 |

FOREIGN PATENT DOCUMENTS

| WO | WO 2009079529 A2 * | 6/2009 |
| WO | WO2012/100345 | 8/2012 |

OTHER PUBLICATIONS

Dubeau et al., "Properties of CsnR, the transcriptional repressor of the chitosanase gene, csnA, of *Streptomyces lividans*", Journal of Bacteriology, vol. 193, No. 10, pp. 2441-2450, May 2011.*
Dubeau et al., "Modification of genetic regulation of a heterologous chitosanase gene in *Streptomyces lividans* TK24 leads to chitosanase production in the absence of chitosan", Microbial Cell Factories, 2011 10:7; pp. 1-10, published Feb. 10, 2011.*
Dubeau et al., "Cytosine deaminase as a negative selection marker for gene disruption and replacement in the genus *Streptomyces* and other actinobacteria", Applied and Environmental Microbiology, vol. 75, No. 4, pp. 1211-1214, Feb. 2009.*

(Continued)

*Primary Examiner* — Rebecca Prouty
*Assistant Examiner* — Richard Ekstrom
(74) *Attorney, Agent, or Firm* — Jenkins, Wilson, Taylor & Hunt, P.A.

(57) ABSTRACT

The present invention relates to genetically modified actinobacteria for the production of an enzyme having chitosanase activity. The genetically modified actinobacteria have a reduced (or abolished) activity of the CsnR polypeptide. Such reduced activity can be obtained by reducing the capacity of expressing the csnR gene, its corresponding transcript or expressing a dominant-negative CsnR polypeptide. Such genetically modified actinobacteria are less dependent (and, in some embodiment, totally independent) on the presence of chitosan in the culture medium for producing an enzyme having chitosanase activity. In addition, the genetically modified bacteria produce less proteases in the culture medium and ultimately provide a chitosanase end-product with higher purity.

19 Claims, 11 Drawing Sheets

| Microorganism | Gene name / Annotation | Function | Pos. | Sequence |
|---|---|---|---|---|
| K. sp. N106 | csnN106 | Chitosanase GH46 | -65 | tcaatctagttaggaaactttcctaactct (SEQ ID NO:74) |
| S. sp. N174 | csnN174 | Chitosanase GH46 | -58 | ttgaatcggttaggaaagtttcctaactct (SEQ ID NO:75) |
| S. coelicolor | SCO0677 | Chitosanase GH46 | -59 | cctcttctgqtaggaaactttcctatcagt (SEQ ID NO:76) |
| S. lividans | csnA / SSPG_06922 | Chitosanase GH46 | -56 | cttcttctgqtaggaaactttcctatcagt (SEQ ID NO:77) |
| S. avermitilis | SAV_2015 | Chitosanase GH46 | -48 | cgaactctgqtaggaaactttcctaacagt (SEQ ID NO:78) |
| S. avermitilis | SAV_1850 | Chitosanase GH75 | -26 | gcaacatggtaaggaaactttcctaacaga (SEQ ID NO:79) |
| S. scabies | SCAB_86311 | Chitosanase GH5 | -78 | cccttctgttaggaaagtttcctactagt (SEQ ID NO:80) |
| S. griseus | SGR_1341 | Chitosanase GH5 | -53 | tgttaatagacaggaaagtttcccaacact (SEQ ID NO:81) |
| S. avermitilis | SAV_1223 | Exochitosanase GH2 | -56 | tgaatccagttagtaaagtttcctaacttg (SEQ ID NO:82) |
| S. coelicolor | SCO2657 | ROK family regulator | -104 | ctccagccaacaggaaactttcctaacaga (SEQ ID NO:83) |
| S. lividans | csnR / SSPG_04872 | ROK family regulator | -116 | ctccagccaacaggaaactttcctaacaga (SEQ ID NO:84) |
| S. avermitilis | SAV_5384 | ROK family regulator | -82 | ctccaccaataggaaactttcctaacaat (SEQ ID NO:85) |
| S. scabies | SCAB_59491 | ROK family regulator | -29 | tggcatccgacaggaaagtttcctaacagt (SEQ ID NO:86) |
| S. griseus | SGR_4874 | ROK family regulator | -64 | ctcaaccgaataggaaactttcctaacaga (SEQ ID NO:87) |

(SEQ ID NO:86)

(56) References Cited

OTHER PUBLICATIONS

Lacombe-Harvey et al., "Accessory active site residues of *Streptomyces sp. N174 chitosanase*. Variations on a common theme in the lysozyme superfamily", FEBS Journal, 276: 857-869, 2009.*

Masson et al., "Factors governing an efficient chitosanase production by recombinant *Streptomyces lividans* strains carrying the cloned chs gene from *Streptomyces* N174", Chitin Enzymology, ed. R.A.A. Muzzarelli, Eur. Chitin Soc., Ancona, pp. 423-430, 1993.*

Masson et al., "Effect of regulatory sequence substitution on chitosanase production from a cloned gene in *Streptomyces lividans*", Chitin World, ed. Z.S. Karnicki, M.S. Brzeski, P.J. Bykowski and A. Wojtasz-Pajak, Sea Fisheries Institute, Gdynia, Poland, pp. 311-320, 1994.*

Bueno et al., "Nucleotide sequence of a 1,3-1,4-β-glucanase-encoding gene in *Bacillus circulans* WL-12," Nucleic Acids Research. vol. 18, No. 14 p. 4248 (1990).

Bueno et al., "Synthesis and Secretion of a *Bacillus circulans* WL-12 1,3-1,4-β-D-Glucanase in *Escherichia coli*," Journal of Bacteriology. vol. 172, No. 4 pp. 2160-2167 (1990).

Carrillo, H., and Lipman, D., "The Multiple Sequence Alignment Problem in Biology," SIAM J. Applied Math. vol. 48, No. 5 pp. 1073-1082 (1988).

Côté et al., "Two exo-β-D-glucosaminidases/exochitosanases from actinomycetes define a new subfamily within family 2 of glycoside hydrolases," Biochemical Journal. vol. 394 pp. 675-686 (2006).

Emanuelsson et al., "Locating proteins in the cell using TargetP, SignalP, and related tools," Nature Protocols. vol. 2, No. 4 pp. 953-971 (2007).

Hoell et al., "Structure and function of enzymes acting on chitin and chitosan," Biotechnology and Genetic Engineering Reviews. vol. 27 pp. 331-366 (2010).

International Search Report corresponding to International Patent Application No. PCT/CA2012/050022 dated May 4, 2012.

Mitsutomi et al., "Chitosanase activity of the enzyme previously reported at β-1,3-1,4-glucanase from *Bacillus circulans* WL-12," Biosci. Biotechnol. Biochem. vol. 62, No. 11 pp. 2107-2114 (1998).

Shinoda et al., "Cloning of an endoglycanase gene from *Paenibacillus cookii* and characterization of the recombinant enzyme," Biotechnology Letters. vol. 34, No. 2 pp. 281-286 (2012).

Yoon et al., "Themostable Chitosanase from *Bacillus* sp. Strain CK4: Cloning and Expression of the Gene and Characterization of the Enzyme," Applied and Environmental Microbiology. vol. 66, No. 9 pp. 3727-3734 (2000).

Shinoda et al., "Improved reaction pattern of an endoglycanase from *Paenibacillus cookii* for chitosan oligosaccharide production," Carbohydrate Research. vol. 359, pp. 54-58 (2012).

* cited by examiner

>Pr-WT
CAGGGCCTTGCGCGGTGGTGGGCGTGAACGCTTCAAT CTAGTTAGGAAACTTTCCTAACTCTC (SEQ ID NO:15)

>Pr-Ph
ttgacctttgatgaGGcGGcGtGaGctacaatcaatA TCTAGTTAGGAAACTTTCCTAACTCTC (SEQ ID NO:16)

Fig. 2A

|  |  |  |  |
|---|---|---|---|
| GH46 { | csnN106 | caatctagttaggaaactttcctaactctcc | (SEQ ID NO:17) |
|  | csnN174 | tgaatcggttaggaaagtttcctaactctct | (SEQ ID NO:18) |
|  | SCO0677 | ctcttctggtaggaaactttcctatcagtgc | (SEQ ID NO:19) |
|  | SSPG_06922 | ttcttctggtaggaaactttcctatcagtgc | (SEQ ID NO:20) |
|  | SAV_2015 | gaactctggtaggaaactttcctaacagtac | (SEQ ID NO:21) |
| GH75 — | SAV_1850 | caacatggtaaggaaactttcctaacagaag | (SEQ ID NO:22) |
| GH5 { | SCAB_86311 | cctttctgttaggaaagtttcctactagttc | (SEQ ID NO:23) |
|  | SGR_1341 | gttaatagacaggaaagtttcccaacactgt | (SEQ ID NO:24) |
|  | Consensus | c GttAGGAAAcTTTCCtAacagt | (SEQ ID NO:25) |

Fig. 2B

| Microorganism | Gene name / Annotation | Function | Pos. | Sequence | |
|---|---|---|---|---|---|
| K. sp. N106 | csnN106 | Chitosanase GH46 | -65 | tcaatctagttaggaaactttcctaactct | (SEQ ID NO:74) |
| S. sp. N174 | csnN174 | Chitosanase GH46 | -58 | ttgaatcgttaggaaagtttcctaactct | (SEQ ID NO:75) |
| S. coelicolor | SCO0677 | Chitosanase GH46 | -59 | cctcttctgtggaaactttcctatcagt | (SEQ ID NO:76) |
| S. lividans | csnA / SSPG_06922 | Chitosanase GH46 | -56 | cttcttctgtggaaactttcctatcagt | (SEQ ID NO:77) |
| S. avermitilis | SAV_2015 | Chitosanase GH46 | -48 | cgaactctgtggtaggaaactttcctaacagt | (SEQ ID NO:78) |
| S. avermitilis | SAV_1850 | Chitosanase GH75 | -26 | gcaacatgtaaggaaactttcctaacaga | (SEQ ID NO:79) |
| S. scabies | SCAB_86311 | Chitosanase GH5 | -78 | cccttctgttaggacaggaaagtttcctactagt | (SEQ ID NO:80) |
| S. grisens | SGR_1341 | Chitosanase GH5 | -53 | tgttaatagacaggaaagtttcctaacact | (SEQ ID NO:81) |
| S. avermitilis | SAV_1223 | Exochitosanase GH2 | -56 | tgaatccagttagtaaagtttcctaacttg | (SEQ ID NO:82) |
| S. coelicolor | SCO2657 | ROK family regulator | -104 | ctccagccaacaggaaactttcctaacaga | (SEQ ID NO:83) |
| S. lividans | csnR / SSPG_04872 | ROK family regulator | -116 | ctccagccaacaggaaactttcctaacaga | (SEQ ID NO:84) |
| S. avermitilis | SAV_5384 | ROK family regulator | -82 | ctcccaccaataggaaactttcctaacaat | (SEQ ID NO:85) |
| S. scabies | SCAB_59491 | ROK family regulator | -29 | tggcatccgacaggaaagtttcctaacagt | (SEQ ID NO:86) |
| S. grisens | SGR_4874 | ROK family regulator | -64 | ctcaacgaataggaaactttcctaacaga | (SEQ ID NO:87) |

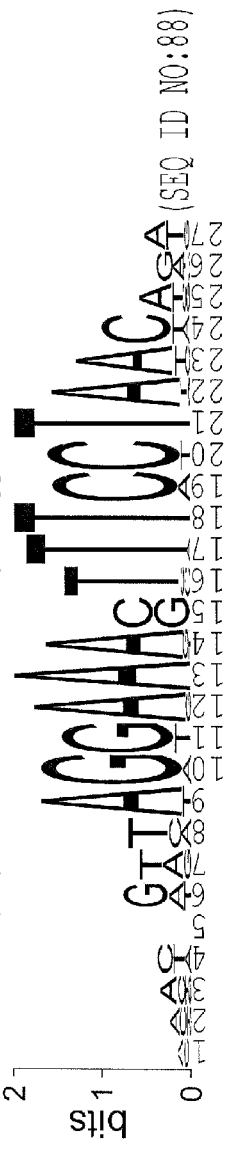

(SEQ ID NO:88)

Fig. 5

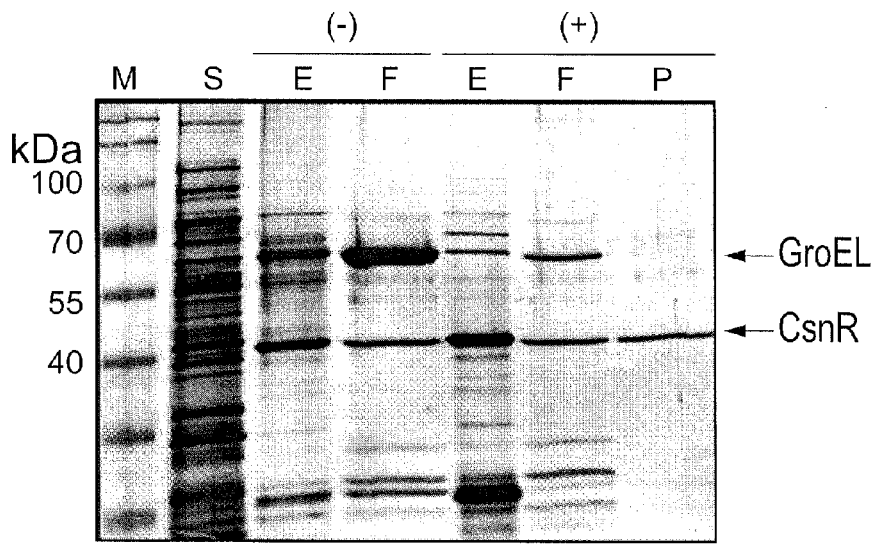
Fig. 6
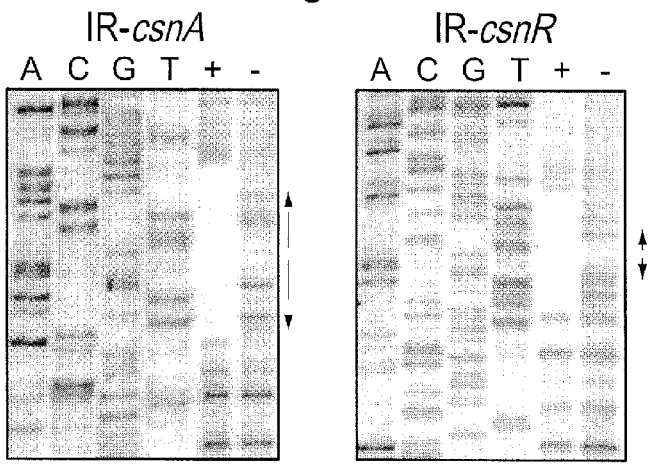
Fig. 7A
IR-*csnA* 15-1-12
cagttcgtgcacgacgggtgcccggcacgcccc|tcttctggtaggaaactttcctatcagt|
gcccggcactcccctcccccactcccccacacctggagattccgtg (SEQ ID NO:89)
IR-*csnR* 17-1-12
cttgacggctcccttgcgggcgggcctacgtt|ctccagccaacaggaaactttcctaacaga|
cgcactcgggcgtcccgccggaacgtgtcccgtgatccgcgcggtggacttcccccaccac
ccctgaaaagctgagcggtcgagaggcaggtg (SEQ ID NO:90)
Fig. 7B

```
SSPG_04872-04871  GAGAGTGCGCTCGCGACCACCCGCGACGAGGTCTTCGACACCTCGCGCTGACCCCGCGC-----
SCO2657-2658      GAGAGTGCGCTCGCGACCACCCGCGACGAGGTCTTCGACACCTCGCGCTGACCCCC-------

SSPG_04872-04871  CACCCCGCGCCACCA----------CCCCGCGCCACCCACTGCCCCA
SCO2657-2658      ---------------CCCCGCGCCACCCCGCGCCACCCACTGCCCCA

SSPG_04872-04871  CCCACCTGTCCCCCGCCCTGCCCCTGGGAGCTTTCGCCATGCCCGGAATATCCAGAAAAGC(SEQ ID NO:91)
SCO2657-2658     CCCACCTGTCCCCC-GCCCTGCCCC-GCCCTGGGAGCTTTCGCCATGCCCGGAATATCCAGAAAAGC(SEQ ID NO:92)
```

CSNR-DEFICIENT ACTINOBACTERIA FOR THE PRODUCTION OF AN ENZYME HAVING CHITOSANASE ACTIVITY

CROSS-REFERENCE TO RELATED APPLICATIONS

This application claims priority to U.S. provisional patent application 61/596,764 filed on Feb. 9, 2012 and herewith incorporated in its entirety.

CROSS-REFERENCE TO RELATED DOCUMENTS

This application comprises a sequence listing filed in electronic form as an ASCII .txt file entitled 140826_ST25, created Feb. 6, 2013, 2000 bytes (20 kilobytes). The content of the sequence listing is incorporated herein in its entirety.

TECHNOLOGICAL FIELD

The present invention relates to cells for the production of a chitosanase as well as methods using these cells for the production of a chitosanase.

BACKGROUND

Chitosanases are enzymes hydrolysing chitosan, a β-1,4 linked D-glucosamine bio-polymer. Chitosan oligosaccharides have numerous emerging applications and chitosanases can be used for industrial enzymatic hydrolysis of chitosan. These extracellular enzymes, produced by many organisms including fungi and bacteria, are well studied at the biochemical and enzymatic level but very few works were dedicated to the regulation of their gene expression.

Chitosan, a partly N-deacetylated form of chitin, is naturally found in the cell walls of fungi, especially in *Zygomycetes* (*Mucor* sp., *Rhizopus* sp.), and in the green algae *Chlorophyceae* (*Chlorella* sp.). Chitosan, is a polysaccharide made of β-1,4-linked D-glucosamine (GlcN) units with a variable content of N-acetyl-D-glucosamine (GlcNAc) units. Chitosan is produced at industrial scale by alkaline deacetylation of chitin, originating mainly from crustacean shells. This polysaccharide, almost unique among natural polymers for its amino groups that remain positively charged in mild acidic solutions, is the subject of numerous works oriented towards its numerous emerging applications in medicine, agriculture, dietetics, environment protection and several other fields. Chitosan is also a valuable source of GlcN, a neutraceutical used as a therapeutic agent in osteoarthritis. Many properties of chitosan, especially in biological applications are dependent on its molecular weight, i.e. on its degree of polymerization.

The very short derivatives of chitosan—the chito-oligosaccharides are of particular interest, due to their increased solubility in aqueous solutions and their specific biological activities. To obtain chitosan chain of varying degrees of polymerization, several chemical and physical techniques were investigated. Enzymatic techniques with either free or immobilized chitinase or chitosanase enzymes are also intensively studied. Chitosanase production has been found in many microorganisms, bacteria or fungi. The enzymes so far characterized at the primary sequence level belong to seven families of glycoside hydrolases: GH3, GH5, GH7, GH8, GH46, GH75 and GH80. While these enzymes are endo-hydrolases, their mechanism could potentially be transformed into exo-type by protein engineering as shown for the GH46 chitosanase from *Bacillus circulars* MH-K1. Chitosan can be also hydrolyzed by enzymes acting by an exo-mechanism generating GlcN monomers. The chitosanases from *Streptomyces* have been widely studied in various aspects of structure-function relationships. Usually, these chitosanases are produced in the heterologous host *Streptomyces lividans* via the multi-copy vector pFD666. However, very few works have been dedicated to the regulation of chitosanase gene expression in the native and/or heterologous hosts. Most studies were limited to the follow up of chitosanase production in various culture media. An efficient production of CsnN106 or CsnN174 chitosanases in *Streptomyces lividans* TK24 is strictly dependent on the addition of chitosan or its derivatives to the culture medium indicating that these foreign genes are still subjected to some kind of chitosan-dependent regulation in the heterologous host. However, the addition of chitosan as a component in any culture medium is not without problems due to the well known anti-microbial properties of this polysaccharide which can slow down the bacterial growth.

Microbiological studies and the analysis of sequenced genomes showed that chitosanases are widespread among filamentous fungi and Gram-positive bacteria, particularly in bacilli and actinobacteria. In *Streptomyces*, well-studied chitosanases belong to glycoside hydrolase families GH2, GH5, GH46, and GH75. Putative chitosanases from these families, as well as from GH8 (characterized mainly from Gram-positive bacili) are found in many recently sequenced actinomycete genomes (CaZy database). *Streptomyces lividans* is an actinomycete isolated from soil, commonly used as heterologous host for production of proteins in an extracellular mode, including the well-studied chitosanase from *Streptomyces* sp. N174 (CsnN174). Until the publication of the genome sequence of *S. coelicolor* A3(2) and, more recently, of the *S. lividans* genomic contigs (GenBank accession no. ACEY01000), these two closely related species were thought to be devoid of chitosanase activity because they grew very poorly on media with chitosan and no chitosanase activity was detected in their cultures. However, genes encoding putative chitosanases of the GH46 family are present in both genomes: SCO0677 (csnA) and SCO2024 (csnB) in *Streptomyces coelicolor* A3(2) and the almost identical genes SSPG_06922 (genomic coordinate 7.62 Mb) and SSPG_05520 (genomic coordinate 6.14 Mb) in *S. lividans* TK24. The biochemical properties of CsnA from *S. coelicolor* A3(2) have been studied in detail recently. In vivo studies performed with *S. lividans* TK24 have shown that CsnA is produced at a very low level (in the range of milliunits per ml), explaining the lack of chitosanase detection by earlier, less-sensitive techniques. Despite this low expression level, the deletion of csnA resulted in increased sensitivity to the antimicrobial effect of chitosan. While there are numerous reports on biochemical properties of chitosanases, knowledge about the regulation of chitosanase gene expression is very scarce. In contrast, the genetic regulation of the degradation of chitin, the N-acetylated form of chitosan, has been extensively studied in *Streptomyces*. Members of this genus play an important part in chitin degradation in soil and produce a wide array of chitinases and chitin-binding proteins. The regulation of chitinase (chi) gene expression in *Streptomyces* is rather complex, and as many as four different mechanisms have been identified, some of them linked to more general phenomena such as carbon catabolite repression, antibiotic production, and morphogenesis through the chitin-derived monomer N-acetyl-D-glucosamine (GlcNAc). The Cpb1 regulator controls the expression of the chiA gene in *S. lividans*. The two-component system ChiS/ChiR participates to the genetic regulation of chiC gene of *S. coelicolor*. Reg1, the negative regulator of α-amylase genes in *S. lividans*, seems also to be involved in the genetic regulation of chitinase genes. Finally DasR, a member of the HutC/GntR subfamily, regulates the expression of some chitinase genes through interaction with the dre motif in *S. coelicolor*. DasR also has a more global effect on other genes involved in GlcNAc metabolism.

It would be highly desirable to be provided with an expression system for a chitosanase which is not dependant on the presence of chitosan in the culture medium. It would be desirable to be provided with an expression system which would allow for the expression of endogenous as well as exogenous chitosanase. It would also be highly desirable to be provided with an expression system for a chitosanase which limits or avoids the production of protease in the culture medium. It would further be desirable, for pharmaceutical applications, to be provided with an expression system for a chitosanase which can be cultured in a defined medium.

BRIEF SUMMARY

The present invention concerns the use of a genetically modified actinobacterium host for the production of a chitosanase in the absence of chitosan.

In a first aspect, the present invention provides a genetically modified actinobacterium cell for the production of an enzyme having chitosanase activity, said genetically modified actinobacterium cell having a reduced activity of a native CsnR polypeptide when compared to the activity of said native CsnR polypeptide in a native actinobacterium cell. The CsnR polypeptide may be encoded by a csnR gene or one of its ortholog. In an embodiment, the actinobacterium cell is a *Streptomyces*, such as, for example, a *Steptomyces lividans*. In another embodiment, the enzyme has an exo-chitosanase activity, such as those represented in the glycoside hydrolase (GH) 2 family. In another embodiment, the enzyme has an endo-chitosanase activity, such as those represented in the glycoside hydrolase (GH) 5, 8, 46 or 75 family. In still another embodiment, the enzyme further comprises at least one additional enzymatic activity: a beta-1,4-glucanase activity (encompassing cellulose activity) and/or a licheninase activity. In still another embodiment, the enzyme is exogenous to the genetically modified actinobacterium cell. In yet a further embodiment, the enzyme is encoded by a nucleic acid vector, such as, for example, an integratable vector. In yet another embodiment, the enzyme is endogenous to the genetically modified actinobacterium cell. In another embodiment, an open-reading frame of a csnR gene is disrupted in the actinobacterium host. In still another embodiment, a fragment of the csnR gene is deleted in the actinobacterium host. In yet another embodiment, an exogenous nucleic acid molecule is inserted in the open-reading frame of the csnR gene in the actinobacterium host. In another embodiment, a complete csnR gene is deleted in the actinobacterium host.

In a second aspect, the present invention provides a method for producing an enzyme having chitosanase activity. Broadly the method comprises (i) placing the genetically modified actinobacterium cell as described herein in a culture medium devoid of chitosan, chitosan fragments or chitosan derivatives and (ii) culturing the genetically modified actinobacterium cell under conditions suitable for the production of the chitosanase. In an embodiment, the method further comprises (iii) purifying the chitosanase from the culture medium. In another embodiment, the culture medium comprises malt extract, $KH_2PO_4$, $K_2HPO_4$, $(NH_4)_2SO_4$ and $MgSO_4$. In another embodiment, the culture medium consists of malt extract, $KH_2PO_4$, $K_2HPO_4$, $(NH_4)_2SO_4$ and $MgSO_4$.

In a third aspect, the present invention provides a method of reducing the molecular weight of a chitosan molecule. Broadly the method comprises contacting the enzyme produced by the method described herein with said chitosan molecule under conditions sufficient to allow the cleavage of said chitosan molecule by said enzyme.

In a fourth aspect, the present invention provides a method of producing a low-molecular weight chitosan. Broadly, the method comprises contacting the enzyme produced by the method as described herein with a chitosan molecule under conditions sufficient to allow the cleavage of said chitosan molecule by said enzyme into said low molecular weight chitosan.

In a fifth aspect, the present invention provides a method of producing a chitosan oligosaccharide. Broadly, the method comprises contacting the enzyme produced by the method described herein with a chitosan molecule under conditions sufficient to allow the cleavage of said chitosan molecule by said enzyme into said chitosan oligosaccharide.

BRIEF DESCRIPTION OF THE DRAWINGS

Having thus generally described the nature of the invention, reference will now be made to the accompanying drawings, showing by way of illustration, a preferred embodiment thereof, and in which:

FIG. 2. Characterization of promoter regions. (A) Fragment of the promoter region of csnN106 gene variants. Pr-WT: native promoter region, the putative −35 (nucleotides between positions 8 to 13 of SEQ ID NO: 1) and −10 (nucleotides between positions 32 and 37 of SEQ ID NO: 1) boxes are indicated in blue. Pr-Ph: a construct in which the native promoter has been replaced by a double promoter from *Streptomyces ghanaensis* phage I19, the respective −35 and −10 boxes are over and underlined. Low case letters indicate nucleotide changes between Pr-WT and Pr-PH. (*): start points of transcription. Arrows: inverted repeats of the palindromic box. (B) Alignment of palindromic sequences present in the promoter regions of chitosanase genes in actinomycetes. Nucleotides are numbered relative to the center of symmetry. In the consensus sequence of SEQ ID NO: 11, nucleotides at positions 9 and 13 are identified as critical for interaction; nucleotides at positions 2 to 6, 8, 10, 12, 14 and 16 to 20 are identified as moderately important for interaction; whereas the other nucleotides are identified as without apparent effect on interaction. (↑): base pairs mutated in the Pr-Pa construct. GH: glycoside hydrolase family.

FIG. 5. Alignment of palindromic sequences found upstream of genes encoding chitosanases or ROK family regulator genes in actinomycetes and LOGO representation of consensus sequence. "Pos." (position) indicates the distance in by from the central nucleotide of the palindromic sequence to the start codon of the associated gene. K. sp. N106=*Kitasatospora* sp. N106; S. sp. N174=*Streptomyces* sp. N174.

FIG. 6. Purification of CsnR. Protein samples from each stage of the CsnR purification were analyzed by 10% SDS-PAGE and visualized after silver nitrate staining. M, PageRuler prestained molecular mass protein ladder (Fermentas); S, soluble fraction of cell lysate from recombinant *E. coli* induced with 0.1 mM IPTG; (−), purification attempt without previous treatment of the soluble fraction of cell lysate; (+), purification steps with a previous 2 mM ATP and 5 mM MgCl2 treatment of the soluble fraction of cell lysate; E, eluate collected from the glutathione-Sepharose 4B resin following a 4-h incubation with specific protease; F, 20 microliter of the size exclusion chromatography fraction with the highest GroEL contamination; P, 20 microliter of pooled size exclusion chromatography fractions with purified CsnR.

FIG. 7. DNase I footprinting analysis of the CsnR binding site to csnA and csnR promoters. (A) A 298-bp labeled probe (csnA-IR) and a 256-bp labeled probe (csnR-IR), both including the entire intergenic regions upstream from csnA and csnR, respectively, were subjected to partial DNase I digestion in the presence (+) or absence (−) of ~0.5 nmol of purified CsnR. Vertical arrows correspond to the palindromic sequence shown in panel B. (B) Partial intergenic region sequences upstream of csnA and csnR. Boxes correspond to the protected region in panel A. Arrows correspond to the palindromic sequence. Boldface gtg represents the translation initiation codon. **, transcription initiation site as determined by primer extension. The −35 and −10 boxes of the deduced promoter sequence are shown in italic.

FIG. 12. Sequence alignment of the sequenced intergenic region between SSPG_04872 (csnR) and SSPG_04871 (csnE) and the published intergenic region between SCO2657 (csnR homologue) and SCO2658 (csnE homologue). Green highlight correspond to the stop codon of SSPG_04872 and SCO2657 and the translation initiation codon of SSPG_4871 and SCO2658. Yellow highlight correspond to direct repeats. Underlined base pairs correspond to the putative ribosome binding site.

DETAILED DESCRIPTION

Definitions

Figure 1:
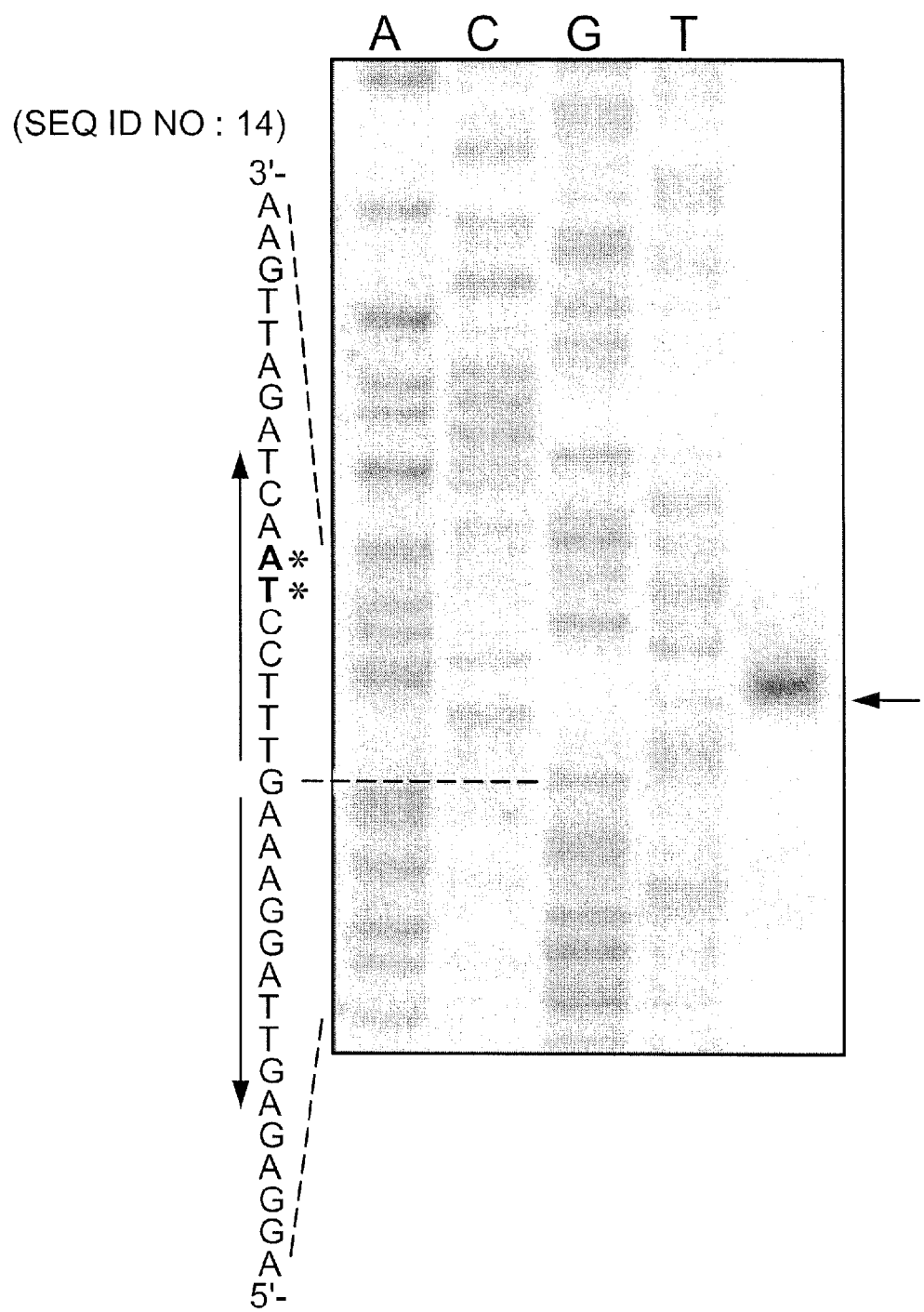
FIG. 1. Primer extension analysis of csnN106 transcripts. The apparent 5' terminus for the csnN106 transcript was identified by annealing a radiolabeled primer complementary to the mRNA of csnN106 and extension with reverse transcriptase. 40 μg of total RNA, from GlcN-chitosan oligomers induced *S. lividans* TK24(pHPr-WT), were used for extension reaction. The same primer was used for DNA sequencing reactions with the pHPr-WT plasmid. (→): primer extension product; (*): apparent transcription start site. Vertical arrows: palindromic sequence.

"Actinobacterium cell" or "Actinobacteria". As used herein, the terms "Actinobacterium cell", "Actinobacteria" or "Actinomycete" are used interchangeably to refer bacteria of the Actinobacteria class. This class includes, but is not limited to the following subclasses (and orders): Acidimicrobidae (Acidimicrobiales), Coriobacteridae (Coriobacteriales), Nitriliruptoridae (Nitriliruptorales, Euzebyales), Rubrobacteridae (Rubrobacterales, Solirubrobacterales, Thermoleophilales), and Actinobacteridae, (Bifidobacteriales or Actinomycetales). Specific genera of actinobacteria include, but are not limited to, *Streptomyces* (such as, for example, *Streptomyces lividans*), *Amycolatopsis*, *Catenulispora*, *Kitasatospora*, *Verrucosispora*, *Micromonospora*, *Thermobispora*, *Salinispora*, *Streptosporangium*, *Actinoplanes*, *Nocardiopsis*, *Stackebrandtia*, and *Saccharopolyspora*.

In the context of the present invention, an actinobacterium cell is also understood to express, in its native state (e.g. when it is not genetically engineered), the csnR gene (or one of its ortholog), its corresponding transcript and polypeptide. As such, a "native" actinobacterium cell is understood to refer to a wild-type, non-genetically engineered bacteria expressing the csnR gene (or its ortholog) and producing the corresponding polypeptide (CsnR for example). Native actinobacteria include, but are not limited to *Streptomyces* (such as, for example, *Streptomyces lividans*), *Amycolatopsis, Catenulispora, Kitasatospora, Verrucosispora, Micromonospora, Thermobispora, Salinispora, Streptosporangium, Actinoplanes, Nocardiopsis*, and *Stackebrandtia, Saccharopolyspora*.

When an actinobacterium cell is qualified as being "genetically engineered", it is understood to mean that it has been manipulated to either add a specific exogenous nucleic acid molecule and/or removed a specific endogenous nucleic acid molecule. The manipulation did not occur in nature and is the results of in vitro manipulations of the actinobacterium cell. In an embodiment, the genetic manipulations is limited to the cnsR gene (or its ortholog), its corresponding transcript or its corresponding polypeptide and are intended to either reduce the expression of the gene, reduce the expression and/or stability of the transcript, reduce the expression and/or stability of the polypeptide or reduce the functionality of the polypeptide. In one embodiment, the open-reading frame of the csnR gene (or its ortholog) is disrupted specifically by the introduction of an exogenous nucleic acid molecule.

"Antisense oligonucleotide". This term is understood to mean an oligonucleotide which is wholly or partially complementary to, and can hybridize with, a target nucleic acid (either DNA or RNA) having the sequence the csnR gene (or its ortholog) or its corresponding transcript. For example, an antisense nucleic acid or oligonucleotide comprising 10, 15 or 20 nucleotides can be sufficient to lower or inhibit expression of the csnR gene (or its ortholog). Alternatively, an antisense nucleic acid or oligonucleotide can be complementary to 5' or 3' untranslated regions, or can overlap the translation initiation codon (5' untranslated and translated regions) of the csnR gene (or its ortholog). In another embodiment, the antisense nucleic acid is wholly or partially complementary to, and can hybridize with, a target nucleic acid that encodes a polypeptide from the csnR gene (or its ortholog). As non-limiting examples, antisense oligonucleotides may be targeted to hybridize to the following regions: mRNA cap region; translation initiation site; translational termination site; transcription initiation site; transcription termination site; polyadenylation signal; 3' untranslated region; 5° untranslated region; 5' coding region; mid coding region; 3' coding region; DNA replication initiation and elongation sites. Preferably, the complementary oligonucleotide is designed to hybridize to the most unique 5' sequence of the csnR gene (or its ortholog), including any of about 15-35 nucleotides spanning the 5' coding sequence.

"Chitosan". As used herein, chitosan (or a "chitosan molecule") is understood to mean a polysaccharide obtained by N-deacetylation of chitin. In industrial scale procedures, chitosan is obtained from chitin by alkali treatment of crustacean shells. Chitosan is also present in nature in the cell walls of some fungi and algae and in insects. Chitosan is mainly composed of β-1,4-linked D-glucosamine units with a variable content of N-acetyl-D-glucosamine units. The percentage of N-acetyl-D-glucosamine units is defined as the degree of N-acetylation of chitosan ("DA"), while the percentage of D-glucosamine units is also called the degree of deacetylation ("DDA") of chitosan. Most commercial preparations of chitosan are characterized by DDA values between 70 and 99%.

Chitosan is unique among polysaccharides because it carries amino groups which are positively charged in mildly acidic aqueous solution (pH<6.2). Most biological properties of chitosan result from the presence of these positively charged groups. The amino groups can also be coupled to various chemical groups, resulting in a large family of chitosan derivatives.

Since chitosan is a large molecule, its size can be reduced to provide chitosan "fragments". Such fragments includes, but are not limited to low molecular weight chitosan (usually between 5 and 100 kDa) or chitosan oligosaccharides (usually between 0.4 and 5-10 kDa). Such fragments can be obtained through chemical cleavage, but more preferably through the enzymatic action of a chitosanase.

"Chitosanase activity". As used herein, the term "chitosanase activity" or "chitosanase" is intended to refer to the ability of a glycoside hydrolase to cleave a chitosan molecule. Even though a glycoside hydrolase can have more than one enzymatic activity, in the context of the present invention, an enzyme considered to be a chitosanase has more activity towards a chitosane molecule than any other glucoside molecule. In an embodiment, the chitosanase is secreted extracellularly by the native host. The chitosanase can be derived from various organisms, but in an embodiment, the chitosanase is of bacterial origin. In another embodiment, the expression of the contemplated chitosanase is regulated by CsnR (or a polypeptide encoded by a csnR gene ortholog). The contemplated chitosanase possesses an operator recognized by the CsnR polypeptide or a polypeptide encoded by a csnR gene ortholog and such recognition leads to the reduced expression of the chitosanase-encoding gene.

The contemplated enzymes can be divided into two groups based on their biochemical activity: "exo-chitosanase" and "endo-chitosanase". The enzyme having exo-chitosanase activity (also referred to as exo-1,4-beta-D-glucosaminidase) are known to act specifically on chitosan and chitosan oligosaccharides and do not hydrolyze α- or β-glucosides, galactosides, N-acetylglucosaminides including substrates such as colloidal chitin, cellulose, carboxymethylcellulose or cello-oligosaccharides. Known enzymes having exo-chitosanase activity whose expression is regulated by CsnR or a polypeptide encoded by a csnR ortholog belong to the GH2 family of glycoside hydrolase Exemplary exo-chitosanases include, but are not limited to CsxA (or AorCsx from *Amycolatopsis orientalis*) and SAV1223 (*Streptomyces avermitilis*).

On the other hand, the enzyme having endo-chitosanase activity is known to mediate the endohydrolysis of beta-1,4-linkages between residues in a partly acetylated chitosan. The endo-chitosanase includes, but is not limited to, the enzymes belonging to the following families of glycoside hydrolase: GH5, GH8, GH46, GH75, GH80. In some embodiment, the enzyme having endo-chitosanase activity can also present additional enzymatic activity, such as, for example, cellulase and/or licheninase activity. Exemplary endo-chitosanases include, but are not limited to CsnN106 (*Kitasatospora* sp. N106; formerly known as *Nocardioides* sp. N106), CsnN174 (*Streptomyces* sp. N174), CsnA (SCO0677 or ScCsn46A) from *Streptomyces coelicolor* A3(2)), CsxA (or SAV1223) from *Streptomyces avermitilis*, SAV1850 (or SaCsn75A) from *Streptomyces avermitilis*, SAV2015 (*Streptomyces avermitilis*), SCAB_86311 (or SscGH5 from *Streptomyces scabies* 87.22), SGR_1341 (or SgrGH5 from *Streptomyces griseus* IFO13350), SSDG_05015 (or SprGH5 from *Streptomyces pristinaespiralis* ATCC 25486), CsnA (or SliCsn or SSPG_06922 from *Streptomyces lividans*), and/or AA4 GH8 (or =SSMG_06552 from *Streptomyces* sp. AA4).

"csnR gene". This term is understood to mean a gene encoding a negative transcriptional regulator of the ROK family mediating its effect on the chitosanase gene expression of actinobacteria. In actinobacteria, this transcription factor was shown to interact with the operator of the chitosanase-encoding gene and negatively impacts its transcription. The presence of chitosan in the culture medium of the actibacterium cell lessens the affinity of the transcription factor for the operator of the chitosanase-encoding gene and facilitates its transcription (and ultimately its expression). The csnR gene has been described specifically in Streptomyces lividans (SliROK or SSPG_04872).

However, the csnR gene is not limited to the one described in S. lividans and also encompasses all csnR gene orthologs. In the context of the present invention, a "cnsR gene ortholog" is understood to be a gene in a different species that evolved from a common ancestral gene by speciation. In the context of the present invention, a csnR ortholog retains the same function, e.g. it can act as a transcription factor for regulating the expression of chitosanase-encoding genes. Known csnR orthologs include, but are not limited to those described in Streptomyces coelicolor A3(2) (SCO2657), Streptomyces avermitilis (SAV5384), Streptomyces scabies 87.22 (SCAB_59491), Streptomyces griseus IFO13350 (SgrROK or SGR_4874), Streptomyces pristinaespiralis ATCC 25486 (SprROK or SSDG_02817), Streptomyces sp. AA4 (AA4ROK or SSMG_00813), Streptomyces clavuligerus (SCLAV_1826), Streptomyces venezuelae (SVEN_2441), Streptomyces violaceusniger (STRVI_7945) and Streptosporangium roseum (SROS_5819). In an embodiment, the degree of identity of csnR gene ortholog with respect to the csnR gene is at least 60%, 65%, 70%, 75%, 80%, 85%, 90%, 95%, 96%, 97%, 98% or 99% (when determined on the entire open-reading frame of the csnR gene).

As used herein, a "transcript" of the csnR gene (or its ortholog) refers to nucleic acid molecules (most likely mRNA) directed from the csnR gene and encoding the CsnR polypeptide (or the polypeptide encoded by a csnR ortholog). The transcript can be a nucleic acid molecule of transient expression.

"CsnR polypeptide". As used herein, the CsnR polypeptide is understood to refer to the polypeptide encoded by the csnR gene or its ortholog. As indicated above, the "wild-type" or "native" CsnR polypeptide is a transcription factor that can bind to the operator of a chitosanase-encoding gene to modulate (e.g. decrease or repress) its expression. In an embodiment, the CsnR polypeptide (or the polypeptide encoded by a csnR gene ortholog) can bind to the consensus operator sequence of presented in SEQ ID NO:25 and/or the consensus sequence presented in SEQ ID NO:88. In another embodiment, the CsnR polypeptide can bind to any one of the operator sequences presented in SEQ ID NO: 14 to 24 as well as SEQ ID NO: 74 to 87. In yet another embodiment, the CsnR polypeptide is capable of repressing the expression of the chitosanase-encoded gene located downstream of the operator to which it binds. In an embodiment, the CsnR polypeptide (or the polypeptide encoded by a csnR gene ortholog) binds to an operator located at the most at 100 base pairs upstream from the transcription start site. In another embodiment, the CsnR polypeptide or the polypeptide encoded by a csnR gene ortholog) is at least as 50%, 60%, 65%, 70%, 75%, 80%, 85%, 90%, 95%, 96%, 97%, 98% or 99% identical to the polypeptide encoded by the csnR gene of Streptomyces lividans (SliROK or SSPG_04872) when the alignment is performed on the entire length of the compared polypeptides.

A "dominant-negative" CsnR polypeptide is a modified (e.g. non-native) CsnR polypeptide that binds to the operator provided above (any one of those presented in SEQ ID NO: 14 to 25 or 74 to 88) but cannot repress as efficiently the expression of the chitosanase-encoding gene located downstream of the operator as the native CsnR polypeptide. Preferably the affinity of the dominant-negative CsnR polypeptide for the operator is higher than the affinity of the native CsnR polypeptide for the same operator, which will result in the effective displacement (or competition) of the native CsnR polypeptide from the operator of the chitosanase-encoding gene.

"Identity", as known in the art, is a relationship between two or more polypeptide sequences, as determined by comparing the sequences. In the art, identity also means the degree of sequence relatedness between polypeptide/polynucleotide sequences, as the case may be, as determined by the match between strings of such sequences. Identity and similarity can be readily calculated by known methods. The percentage of identity is determined over a specific portion of the nucleic acid/amino acid sequence of the csnR gene (or its ortholog) or CsnR polypeptide (or the polypeptide encoded by a csnR gene ortholog), usually the entire length of the polypeptide sequence. In order to determine the percentage of identity between any amino acid sequences, various tools are known to those skilled in the art. For example, one can use the Protein Blast with the blastp algorithm, a software which is freely accessible through the NCBI's web site (http://blast-.ncbi.nlm.nih.gov/Blast.cgi?PROGRAM= blastp&BLAST_PROGRAMS=blast p&PAGE_TYPE= BlastSearch&SHOW_DEFAULTS=on&LINK_LOC= blasthome).

"Endogenous". In the context of the present invention, an element which is endogenous to an organism is understood to mean that such element is natively provided in the organism. For example, an enzyme having chitosanase activity which is considered endogenous to an actinobacterium cell has been natively produced by such actinobacterium cell and is not the result of a genetic modification by man. As an another example, a nucleic acid molecule which is considered to be endogenous to an actinobacterium cell is considered to have been natively included in or produced by such actinobacterium cell and was not introduced by genetic means from man into the actinobacterium cell.

"Exogenous". In the context of the present invention, an element which is exogenous to an organism is understood to mean that such element is not natively provided in the organism. For example, an enzyme having chitosanase activity which is considered exogenous to an actinobacterium cell is considered not to have been natively produced by such actinobacterium cell. An enzyme that is exogenous was introduced into the actinobacterium cell, most likely through means of genetic modification. As another example, a nucleic acid molecule which is considered to be exogenous to an actinobacterium cell is considered not to have been natively produced by such actinobacterium cell and was introduced (by genetic means) into the actinobacterium cell.

"Nucleic acid vector". As used herein, a "nucleic acid vector" or "vector" is understood to be a nucleic acid molecule which was provided at one point in isolated form and which is used to transfer a nucleic acid molecule from an organism to another. Vectors can be derived from bacterial plasmids or chromosomal segments or mobile genetic elements as well as bacteriophages.

In one embodiment, the transferred nucleic acid molecule can encode a polypeptide (such as, for example, the CsnR polypeptide or a polypeptide encoded by a csnR gene ortholog). Optionally, the sequence of the nucleic acid can be optimized for codon usage and recognition depending on the host cell that is considered for expression of the chitosanase gene and protein. More specifically, the vector can comprise a promoter sequence, preferably located upstream of the nucleic acid encoding the chitosanase. In an embodiment, the promoter sequence can be the native promoter of a chitosanase-encoding gene (or a portion thereof such as, for example, the operator, the ribosome-binding sequence, as well as the transcription termination sequence preventing transcription from an upstream gene). In another embodiment, the vector can also comprise a selection marker to facilitate the identification of host cells carrying the vector and/or a signal peptide sequence directing an efficient secretion into the culture medium. Optionally, the vector can further comprise a fusion peptide or protein or tag, operatively linked to the coding-sequence of the chitosanase.

In another embodiment, the nucleic acid molecule can be provided to achieve the disruption of the csnR gene open-reading frame. In such embodiment, it may be advantageous to provide a vector that is capable of being integrated (e.g. integretable) into the bacterial host genome. In an embodiment, the integration is specific to the csnR gene and can even lead to a deletion in the coding sequence of the gene. Such method is provided in Dubeau et al. (2009).

"microRNA" or "miRNA". This term is understood as a short ribonucleic acid (RNA) molecule found in eukaryotic cells capable of mediating gene silencing. A microRNA molecule has at least 15, 20 or even 22 oligonucleotides. On average, a miRNA has 22 oligonucleotides. miRNAs are post-transcriptional regulators that bind to complementary sequences on target messenger RNA transcripts (mRNAs), usually resulting in translational repression or target degradation and gene silencing. miRNA can be designed to specifically silence the csnR gene (or its ortholog), favor the degradation of its transcript and/or repress the translation of its transcript.

"Operator". As used herein, an "operator" is located immediately upstream of a transcription start site of an open-reading frame and specifically binds a transcription factor which will modulate gene expression of the downstream open-reading frame (and even the entire operon in some embodiments). In the context of the present invention, the csnR operator binds CsnR (or the polypeptide encoded by a csnR gene ortholog). The binding of CsnR (or the polypeptide encoded by a csnR gene ortholog) to the operator diminishes and even represses the expression of the downstream located chitosanase gene. In an embodiment, the consensus sequence of the csnR operator is SEQ ID NO: 25. In an embodiment, the consensus sequence of the csnR operator is SEQ ID NO: 88. In still another embodiment, the specific sequence of the csnR operator is any one of SEQ ID NO: 14 to 24 and SEQ ID NO: 77 to 87.

"Ribozymes". A ribozyme (from ribonucleic acid enzyme, also called RNA enzyme or catalytic RNA) is an RNA molecule that catalyzes a chemical reaction. Ribozymes can play an important role as enzymes which target defined RNA sequences. Ribozymes can be genetically engineered to specifically cleave a transcript of a csnR gene (or its ortholog).

"RNA interference" or "RNAi" is a post-transcriptional gene silencing process that is induced by a microRNA (miRNA) or a double-stranded RNA (or dsRNA (a small interfering RNA; siRNA)) and has been used to modulate gene expression. Generally, RNAi is being performed by contacting cells with a double stranded siRNA or a small hairpin RNA (shRNA). However, manipulation of RNA outside of cells is tedious due to the sensitivity of RNA to degradation. It is thus also encompassed herein a deoxyribonucleic acid (DNA) compositions encoding small interfering RNA (siRNA) molecules, or intermediate siRNA molecules (such as shRNA), comprising one strand of a siRNA. Accordingly, it is herewith provided an isolated DNA molecule, which includes an expressible template nucleotide sequence of at least about 16 nucleotides encoding an intermediate siRNA, which, when a component of a siRNA, mediates RNA interference (RNAi) of a target RNA. It is also contemplated to use of RNA interference (RNAi) to modulate the expression of the csnR gene (or its ortholog) in target cells. The suppression of gene expression caused by RNAi may be transient or it may be more stable, even permanent.

"Small interfering RNA" or "siRNA" refers to any nucleic acid molecule capable of mediating RNA interference "RNAi" or gene silencing. For example, siRNA can be double stranded RNA molecules from about 10 to about 30 nucleotides long that are named for their ability to specifically interfere with protein expression. In one embodiment, siRNAs are 12-28 nucleotides long, more preferably 15-25 nucleotides long, even more preferably 19-23 nucleotides long and most preferably 21-23 nucleotides long. Therefore preferred siRNA are 12, 13, 14, 15, 16, 17, 18, 19, 20, 21, 22, 23, 24, 25, 26, 27, 28 nucleotides in length. As used herein, siRNA molecules need not to be limited to those molecules containing only RNA, but further encompass chemically modified nucleotides and non-nucleotides. siRNA are designed to decrease expression of the csnR gene (or its ortholog) in a actinobacterium cell by RNA interference. siRNAs comprise a sense region and an antisense region wherein the antisense region comprises a sequence complementary to an mRNA sequence for the csnR gene (or its ortholog) and the sense region comprises a sequence complementary to the antisense sequence of the gene's mRNA. A siRNA molecule can be assembled from two nucleic acid fragments wherein one fragment comprises the sense region and the second fragment comprises the antisense region of siRNA molecule. The sense region and antisense region can also be covalently connected via a linker molecule. The linker molecule can be a polynucleotide linker or a non-polynucleotide linker.

"Triplex oligonucleotides". This expression is understood to mean oligonucleotides which will bind to duplex nucleic acid (i.e., DNA:DNA or DNA:RNA), to form a stable triple helix containing or triplex nucleic acid. Such triplex oligonucleotides can inhibit transcription and/or expression of the csnR gene (or its ortholog). Triplex oligonucleotides are constructed using the base-pairing rules of triple helix formation and the nucleotide sequence of the csnR gene (or its ortholog).

Optimized Cells for the Production of an Enzyme Having Chitosanase Activity

The present invention provides an expression system for producing an enzyme having chitosanase activity. Such expression system is based on the use of actinobacteria for the production of the enzyme.

As known in the art, actinobacteria have been shown useful for the production of chitosanase, either of exogenous or endogenous nature. However, and unlike other host cells of non-actinobacterial origin, the production of chitosanase in actinobacteria has been shown to be strictly dependant on the presence of chitosan in the growth medium. As indicated above, the use of chitosan during fermentation is not trivial and impose severe limitations. As shown herein, the dependence on chitosan has been shown to be in part associated with CsnR, a transcription factor which represses the expression of chitosanase-encoding genes. In the presence of chitosan, the affinity of CsnR for the promoter of the chitosan-encoding genes lessens and, ultimately expression of the chitosanase is permitted or augmented. As also shown herein, a reduction in CsnR activity (e.g. for example via a genetic alteration of in the open-reading frame of the csnR gene) resulted in a derepression in the expression of the chitosanase-encoding gene, an absence of dependence towards chitosan in the culture medium for expressing a chitosanase and an increase expression in chitosanase in actinobacteria.

As such, it is contemplated that a genetically modified actinobacterium cell (whose activity in CsnR would be reduced when compared to a non-modified actinobacterium cell) could successfully be used for the production of an enzyme having chitosanase activity. In an embodiment, the genetically modified actinobacterium cell possesses a reduced amount of a native (e.g. functional) CsnR polypeptide when compared to a corresponding wild-type (e.g. native) actinobacterium. In an embodiment, the genetically modified actinobacterium cell does not express any detectable amount of a native (e.g. functional) CsnR polypeptide and/or of a transcript of a csnR gene.

Such reduced or abolished activity of the CsnR polypeptide can be obtained by modifying the csnR gene or its surrounding regions. For example, the 5' and/or 3' untranslated regions of the csnR gene can be modified in such a way that the expression of the csnR gene is reduced or abolished.

Alternatively, it is also possible to disrupt the open-reading frame of the csnR gene directly to mediate this effect. The disruption of the csnR open-reading frame, even by a single nucleotide, will provide mutations which will either introduce a stop codon prematurely or code for a non-functional CsnR polypeptide (or fragment thereof). In an embodiment, the disruption can include the deletion and/or the addition of at least one nucleotide in the csnR gene open-reading frame. The disruption can include the deletion and/or the addition of a fragment of in the csnR gene open-reading frame. In an embodiment, this fragment is at least 700 base pairs, at least 728 base pairs or at least 774 base pairs. The disruption can also concern the deletion of the entire csnR gene's open-reading frame. The genetic disruption of the csnR gene can be mediated through specific integration (and optionally the subsequent specific removal) of a nucleic acid vector (for example an integrating vector).

It is also possible to reduce or abolish the activity or expression of the CsnR polypeptide by reducing the amount and/or the stability of the transcripts of the csnR gene. This may be achieved by providing a nucleic acid tool specific for the transcript of the csnR gene which will reduce the stability of the transcript and ultimately limit the amount of the transcript. Such nucleic acid tools include, but are not limited to, antisense oligonucleotides, small interfering oligonucleotides, ribozymes, oligonucleotides capable of forming triplex oligonucleotides and double stranded RNA.

In yet another embodiment, it is possible to reduce or abolish CsnR activity in the actinobacteria by introducing a dominant-negative CsnR polypeptide in the cell host. Such dominant negative CsnR polypeptide can reduce the repression at the chitosanase-encoding gene's operator and as such facilitate the expression of the chitosanase gene.

The genetically modified cell described herewith can be useful for the production of an enzyme which is either endogenous or exogenous to the cell. As shown in Examples I and III, exogenous enzymes have been successfully produced in a genetically modified actinobacterium cell as described herein. As shown in Example II, endogenous enzymes have been successfully produced in a genetically modified actinobacterium cell as described herein.

When an exogenous chitosanase is expressed in the genetically modified bacterium, it can be provided on a nucleic acid vector to be introduced into the bacterial host. The vector encoding the chitosanase can either multiply independently in the bacterial host (in the form of a plasmid for example) or can be integrated into the host's genome for increased genetic stability. In an embodiment, the nucleic acid vector comprises not only the chitosanase-encoding gene but also the promoter associated thereto (including, in some embodiments, the operator which is specifically recognized by CsnR or a polypeptide encoded by a csnR gene ortholog), especially the ribosome-binding sequence and, optionally, a transcription termination sequence preventing transcription from an upstream gene.

Methods for Producing the Enzyme Having Chitosanase Activity

The present invention provides optimized methods and processes for producing chitosanase from an actinobacterium cell. In order to do so, the actinobacterium cell described above is first placed in a culture medium in the absence of (devoid of) chitosan, chitosan fragments or chitosan derivatives. As such, no exogenous chitosan, chitosan fragments or chitosan derivatives have been added to the culture medium nor can chitosan, chitosan fragments or chitosan derivatives can be detected in the culture medium.

The actinobacterium is then cultured in conditions favorable for chitosanase gene expression, and, ultimately, chitosanase production. Such conditions can include temperature control, shaking, etc.

Even though the production of a chitosanase by the genetically modified actinobacterium has been observed in various media, it is possible to successfully optimize the culture medium used to obtain superior results. One of the culture medium that can be used comprises malt extract, $KH_2PO_4$, $K_2HPO_4$, $(NH_4)_2SO_4$ and $MgSO_4$. The malt extract can be present at a concentration (w/v) between 0.5 and 2 (preferably 2%). The $KH_2PO_4$ can be provided at a concentration (w/v) between 0.1% and 0.4% (preferably 0.4%). The $K_2HPO_4$ can be provided at a concentration (w/v) between 0.5% and 2.2% (preferably 2.2%). The $(NH_4)_2SO_4$ can be provided at a concentration (w/v) between 0.1% and 0.6% (preferably 0.56%). The $MgSO_4$ can be provided at a concentration (w/v) between 0.02% and 0.125% (preferably 0.125%). The pH of the resulting medium is ideally between 6.5 and 7.0 (preferably 6.9). In some embodiment, the culture medium can also comprise a selection marker (such as for example an antibiotic) to selectively propagate the genetically modified actibacterium cell.

During the fermentation process, it is possible to monitor chitosanase activity in the supernatant to identify when the enzyme is released from the actinobacterium cell. It is also possible to monitor for the presence of protease(s) in the supernatant to identify is contaminants are present and, ultimately, if the fermentation should be stopped to prevent the degradation of the chitosanase.

The methods/processes described herewith provide a chitosanase end-product which is of relatively high purity (at least 80%, 85%, 90% or 95% purity) and can be used without further purification in an industrial process. However, for some applications, it may be necessary to further purify the chitosanase from the fermentation broth. Such purification can include, but is not limited to, filtration, dialysis, precipitation, affinity-purification (antibody-based or tag-based) and chromatography. In an embodiment, the chitosanase is purified using cation-exchange chromatography.

Optionally, before placing the genetically modified actinobacterium cell in a culture medium, it may be advisable to apply a selective pressure on the initial actinobacterium cell population used to select a genetically modified actinobacterium cell having a reduced CsnR polypeptide activity. Such selective pressure may be associated with a specific genetic trait (such as for example an integration or a deletion in the csnR gene). It may also be necessary, to optimize production, to continue to add the selective pressure during the fermentation process.

Methods of Using the Enzyme Having Chitosanase Activity

The present invention also provides methods of cleaving chitosan molecules to generate either low molecular weight chitosan (usually between 5 and 100 kDa) or chitosan oligosaccharides (usually between 0.4 and 5-10 kDa). The methods presented herein use the chitosanase produced by the genetically engineered actinobacterium cell described herein for reducing the molecular weight of the chitosan. The method presented herein should be conducted under conditions allowing enzymatic activity of the chitosanase. Such condition can include, but are not limited to, temperature, pH, reaction medium, presence of substrate, absence of inhibitors, etc. The method can also optionally comprise a step for the recuperation and purification of the products of the enzymatic reaction (e.g. LMWC or CHOS).

The chitosanase does not need to be purified in order to be used in the method. For example, a sample of a culture medium that was previously cultured with the genetically engineered actinobacterium cell capable of expressing (and preferably secreting) a chitosanase, such as the one described herein, can be used. However, the chitosanase may be purified, in part, in order to be included in the method. Purification means that may be used include, but are not limited to, centrifugation, precipitation, filtration, dialysis, solvent extraction, electrophoresis, lyophilization and/or chromatography (such as, for example, cation-exchange chromatography).

The method is preferably conducted at a temperature optimal for the chitosanase, usually between 30° C. to 40° C. (for reactions lasting between 24 and 120 hours) or between 40° C. and 60° C. (for reactions lasting between 10 min and 6 hours). Higher temperatures facilitate the dissolution of chitosan in aqueous solutions. However, mixtures of chitosan molecules, especially concentrated mixtures of chitosans of lower molecular weight are subjected to the Maillard's reaction at high temperatures, resulting in brownish, chemically altered products which are inadequate for many applications. The occurrence of this reaction sets the upper temperature limits for enzymatic hydrolysis of chitosan at 70° C. to 75° C. for reaction times between 10 min and 6 h and 55° C. to 60° C. for reaction times between 24 hours and 48 hours.

The chitosanase can cleave a variety of different chitosan molecules. Chitosan is a linear polysaccharide composed of randomly distributed β-(1-4)-linked D-glucosamine (deacetylated unit) and N-acetyl-D-glucosamine (acetylated unit). Typically, the chitosan molecules are defined by their length as well as their degree of deacetylation or DDA. Chitosan which are commonly used in the industry usually have a DDA of more than 50%, and usually 70% or more.

The chitosanase retains its enzymatic activity over a relatively large pH range, e.g. between 3.8 and 6.5. The method is preferably performed at a pH between 4.4 and 5.5, the optimal pH of the chitosanase.

The present invention will be more readily understood by referring to the following examples which are given to illustrate the invention rather than to limit its scope.

Example I

CSNR-K.-O. Cells for the Expression of Exogenous Chitosanase

In this example, a study on the genetic regulation of a heterologous chitosanase gene (csnN106) in *Streptomyces lividans* is provided. Two *S. lividans* strains were used for induction experiments: the wild type strain and its mutant (ΔcsnR), harbouring an in-frame deletion of the csnR gene, encoding a negative transcriptional regulator. Comparison of chitosanase levels in various media indicated that CsnR regulates negatively the expression of the heterologous chitosanase gene csnN106. Using the ΔcsnR host and a mutated csnN106 gene with a modified transcription operator, substantial levels of chitosanase could be produced in the absence of chitosan, using inexpensive medium components. Furthermore, chitosanase production was of higher quality as lower levels of extracellular protease and protein contaminants were observed. This new chitosanase production system is of interest for biotechnology as only common media components are used and enzyme of high degree of purity is obtained directly in the culture supernatant.

Material and Methods

Bacterial Strains and General Culture Conditions.

*E. coli* strain DH5α™ (Invitrogen) was used for cloning experiments and DNA propagation. *E. coli* DH5α™ was grown on Luria-Bertani broth supplemented with 500 µg/ml hygromycin (Hm) or 50 µg/ml kanamycin (Km). Standard methods were used for *E. coli* transformation, plasmid isolation and DNA manipulation. *Streptomyces lividans* TK24 and *S. lividans* ΔcsnR (Dubeau et al., 2009) were used as hosts for chitosanase genes. Preparation of *S. lividans* protoplasts and transformation using rapid small-scale procedure and R5 regeneration medium were performed as described previously (Kieser et al., 2000). After DNA transfer, hygromycin or kanamycin-resistant colonies were selected after addition of 5 mg Hm or Km to 2.5 ml of soft agar overlay. Transformants were chosen following two subsequent cycles of purification on solid yeast/malt extract (YME) medium (Kieser et al., 2000) with 250 µg/ml Hm or Km. Sporulation was obtained by heavy inoculation of SLM3 agar medium plates (Dewitt, 1985). Spores were collected with glass beads and stored in 20% glycerol at −20° C.

Gel Mobility Shift Assay.

$10^8$ spores of *S. lividans* TK24 or *S. lividans* ΔcsnR were inoculated into 50 ml of Tryptic soy broth (TSB, Difco) and grown for 64 h at 30° C. with shaking. Cultures were centrifuged, the mycelial pellets were washed with sterile 0.9% saline and suspended in two volumes of saline. Then, 1 mpv (equivalent of 1 ml of pellet volume) was added to 100 ml of induction medium. Induction medium is a modified M14 medium (M14M) (Pagé et al., 1996) composed of 0.1% $KH_2PO_4$, 0.55% $K_2HPO_4$, 0.14% $(NH_4)_2SO_4$, 0.1% of trace elements solution (2 g/L $CoCl_2.7H_2O$, 5 g/L $FeSO_4.7H_2O$, 1.6 g/L $MnSO_4.H_2O$, 1.4 g/L $ZnSO_4.7H_2O$), pH 6.9. Before use, 0.03% $MgSO_4$, 0.03% $CaCl_2$, 0.125% GlcN and 0.375% chitosan oligomers (1:1 dimer-trimer mix) was added to the M14M. Cultures were incubated at 30° C. with shaking. Every 24 h, 10 ml of culture were collected and centrifuged and pellets were kept frozen at −80° C. Pellets were melted on ice, washed with cold extraction buffer (50 mM Tris, 60 mM NaCl, 5% glycerol, 1 mM EDTA, 1 mM DL-dithiothreitol (DTT), pH 8.0) and suspended in 1 ml of extraction buffer containing a protease inhibitor cocktail (Complete™; Roche Molecular Biochemicals). The bacterial cells were then disrupted by sonication with one treatment of 40 s at 40% amplitude (Vibra-Cell™, 130 Watt 20 kHz, Sonics and materials inc., USA). Total protein extracts were centrifuged at 3000 g for 10 min at 4° C. Supernatants were then frozen and stored at −80° C. until used.

The double-stranded csnN106 palindromic probe (MP12F) was prepared by complementary oligonucleotide annealing and end-labeling with $[\gamma^{-32}P]$ATP (PerkinElmer) and T4 polynucleotide kinase as described by Dubeau et al. (2009). DNA binding reactions (24 µl) contained 10 mM HEPES (pH 7.9), 10% glycerol, 0.2 mM EDTA, 0.5 mM PMSF, 0.25 mM DTT, 1 µg poly(dI-dC), 150 mM KCl, 0.1 nM of labeled probe and 10 µg of protein crude extract. The reaction mixtures were incubated at room temperature for 15 min and then subjected to electrophoresis in a pre-run gel of 6% polyacrylamide (10 mM Tris, 80 mM glycine, 0.4 mM EDTA, pH 8.3). The gel was dried and viewed with a Phosphorimager™ (Molecular Dynamics).

Vector construction. The csnN106 gene fragment (GenBank accession number L40408.1) was amplified by PCR reaction using FwcsnN106 and RvcsnN106 primers (Table 1) and plasmid pCSN106-2 as template (Masson et al., 1995). The amplified SphI-HindIII fragment was cloned into the vector pFDES (Lacombe-Harvey et al., 2009) digested with the same enzymes, giving plasmids pFDES-csnN106. The promoter region of csnN106 (Pr-WT) was PCR-amplified with primers FwPr-WT and RvPr-WT. Purified PCR fragment was cloned between BamHI and SphI restriction sites of pFDES-csnN106 generating pFPr-WT. A mutated version of Pr-WT with two base-pairs substitutions in the palindromic operator (Pr-Pa) was obtained with the PCR-directed mutagenesis method (Ho et al., 1989) using SEQ. 1, Rv1Pr-Pa, Fw2Pr-Pa and RvcsnN106 as primers (Table 1) and the pFPr-WT plasmid as DNA template. The mutated PCR product was digested with BamHI and SphI and cloned into pFDES-csnN106 generating pFPr-Pa. The phage-type version of csnN106 promoter (Pr-Ph) was obtained by annealing two short DNA segments:

```
                                                 (SEQ ID NO: 1)
5'ATCCTGACGGCCCGTCCGCCCAGCGGTACGAGGGCCCCGACCGGAGTT

CCGGTCGGGGCCTTTCGCATGACCGCGCGGGCAAACATGGCGCTTGACCT

TGATGAGGCGGCGTGAGCTACAATCAATATCTAGTTAGGAAACTTTCCTA

ACTCTCCTCATGGGTCCGGAGACCCGCATG3'
``` and

```
                                                 (SEQ ID NO: 2)
5'CGGGTCTCCGGACCCATGAGGAGAGTTAGGAAAGTTTCCTAACTAGAT

ATTGATTGTAGCTCACGCCGCCTCATCAAGGTCAAGCGCCATGTTTGCCC

GCGCGGTCATGCGAAAGGCCCCGACCGGAACTCCGGTCGGGGCCCTCGTA

CCGCTGGGCGGACGGGCCGTCAG3'.
```

Plasmids were introduced into *S. lividans* strains by transformation and selection with kanamycin for pFDES derivatives carrying neoS as resistance gene. The presence of pFDES derivatives were verified by PCR using primers in Table 1.

Results

Transcription Startpoint Mapping by Primer Extension.

$10^8$ spores of *S. lividans* TK24(pHPr-WT) strain were inoculated into 50 ml of TSB with 50 µg/ml Hm and grown for 64 h at 30° C. with shaking. Chitosanase gene expression was obtained in M14 M medium with GlcN and chitosan oligomers as described for gel mobility shift assay. After 14 h, four culture samples of 10 ml each were collected and mixed immediately with stop solution (0.2 volumes of ethanol-equilibrated phenol, 95:5). Samples were centrifuged for 10 min at 4° C. Bacterial pellets were frozen at −80° C. until lysis. Total RNA extraction was carried out using the Qiagen RNeasy® Mini Kit (Qiagen) with the following modifications. Cell disruption was achieved by sonication with two 30 s burst at 35% amplitude separated with a 15 s cooling period, followed by two phenol-chloroform extractions and one chloroform extraction for cell debris elimination. The on-column DNase treatment was done with the RNase-free DNase set (Qiagen). RNA purity and concentration were assessed in a NanoDrop™1000 spectrophotometer (Thermo Scientific). RNA quality was verified by electrophoresis on agarose gel in 1×MOPS electrophoresis buffer with 0.22 M formaldehyde.

20 pmoles of PE-csnN106 primer (Table 1) were end-labeled with $[\gamma\text{-}32P]$ATP (PerkinElmer) and 20 units of T4 polynucleotide kinase, then purified on a G-25 column (GE Healthcare). Total RNA (40 µg) was hybridized with the end-labeled primer (0.5 pmole) in the presence of 10 mM Tris-HCl pH 8.6, 300 mM NaCl and 1 mM EDTA, in a volume of 22 µl by incubation at 95° C. for 5 min, then 55° C. for 90 min. RNA/primer mix was then precipitated with 200 µl ammonium acetate 1 M and 200 µl isopropanol. The pellet was washed with 70% EtOH, dried and suspended in 10 µl of 10 mM Tris-HCl (pH 8.6), reverse transcriptase buffer (1×, Promega), 10 mM DTT, 1 mM dNTPs, 1 µg actinomycine D, 5 units of AMV reverse transcriptase (Promega) and 20 units of RNAsin (Promega) for a total volume of 20 µl. The reaction mixture was incubated at 45° C. for 60 min and stopped with formamide dye. A sequencing reaction was performed with the end-labeled primer and the ALFexpress™ AutoCycle™ Sequencing Kit (Amersham Biosciences) using manufacturer's recommendations. The primer extension sample and the

TABLE 1

Oligonucleotides used in this study

| Aim of primers | Name | Sequence (5'→3') | SEQ ID NO.: |
|---|---|---|---|
| For csnN106 coding region cloning* | FwcsnN106 | CCGGAGACCCGCATGCCCCGGAC | 3 |
|  | RvcsnN106 | CGGTGCGCCAAGCTTGCGTTCGG | 4 |
| For Pr-WT cloning* | FwPr-WT | GTCTGCGCGGATCCTGACGGCCC | 5 |
|  | RvPr-WT | GTCCGGGGCATGCGGGTCTCCGG | 6 |
| PCR-directed mutagenesis for Pr-Pa cloning** | SEQ.1 | ACAACTTCGTCGCGCACATCCA | 7 |
|  | Rw1Pr-Pa | ATGAGGAGAGTTCGGACAGTTTC | 8 |
|  | Fw2Pr-Pa | GAAACTGTCCGAACTCTCCTCAT | 9 |
|  | RvcsnN106 | TGAGGTCGAAGTTCTTGGCGTT | 10 |
| Presence verification of pFDES derivatives into hosts | SEQ.1 | ACAACTTCGTCGCGCACATCCA | 11 |
|  | T7 promoter | TTAATACGACTCACTATAGGG | 12 |
| For Primer extension | PE-csnN106 | TGGGGTGCTTGAGACGCAT | 13 |

*Bold nucleotides correspond to restriction site
**Bold nucleotide correspond to mutated nucleotide sequence reactions were heated 5 min at 95° C. just before loading on a 6% polyacrylamide sequencing gel. The gel was run, dried, visualised and analyzed by a Phosphorimager™ and the ImageQuant™ Version 5.2 software (Molecular Dynamics).

Chitosanase Production Experiments.

$10^9$ spores of S. lividans strains (WT+pFPr-WT, ΔcsnR+pFPr-Pa) were inoculated into 50 ml of TSB supplemented with 50 µg/ml Km (WT+pFPr-WT and ΔcsnR+pFPr-Pa) and grown for 64 h at 30° C. with shaking. Three types of culture were tested. First, a rich, malt extract-based medium (4×M14M without microelements, 0.12% $MgSO_4$, 2% malt extract) was directly inoculated with a portion of the pre-culture in TSB corresponding to an inoculation proportion of 4 mpv/100 ml. Second, 100 ml of chitosan medium (M14 M, 0.03% $MgSO_4$, 0.03% $CaCl_2$, 0.2% malt extract, 0.8% chitosan flakes (Sigma), 0.2% GlcN) was inoculated with 1 mpv of saline washed pre-culture. Third, 100 ml of GlcN/chitosan oligomer medium (M14 M, 0.03% $MgSO_4$, 0.03% $CaCl_2$, 0.125% GlcN and 0.375% chitosan oligomers) was inoculated with 1 mpv of saline washed pre-culture. For each WT+pFPr-WT and ΔcsnR+pFPr-Pa flasks, 50 µg/ml Km was added. Cultures were done in duplicate and incubated at 30° C. with shaking. 10 ml samples were collected every 24 h. Chitosanase and protease activities and total protein concentration were determined in supernatants.

Biochemical Procedures.

Chitosanase activity was measured using the dyed substrate sRBB-C. Briefly, 50 µl of appropriately diluted culture supernatant were added to 950 µl of soluble Remazol Brilliant Blue chitosan (5 mg/ml in 0.1 M Na-acetate buffer pH 4.5) and the mixture was incubated for 60 min at 37° C. Reaction was stopped with 500 µl of 1.2 N NaOH and cooled on ice for 20 min. After centrifugation, the optical density of supernatant was read at 595 nm and converted into chitosanase activity as described (Zitouni et al., 2010). Protein concentration was estimated by the method of Bradford, with bovine serum albumin as standard. Protease activity was determined with azocasein (Aretz et al., 1989).

By primer extension, the start site for mRNA transcribed from csnN106 was determined (FIG. 1 and FIG. 2A), defining the probable −35 and −10 boxes of the promoter of csnN106 as TTGCGC and TTCAAT with a spacer of 18 nucleotides (shown in blue on FIG. 2A). To test another promoter, described as a "strong" promoter by Labes et al. (1997), the original −35 and −10 boxes of csnN106 gene were substituted with the two tandemly arrayed and overlapping promoters of the Streptomyces ghanaensis phage 119, taking the respective transcription start sites as reference (FIG. 2A).

A palindromic sequence overlaps the transcriptional start site of csnN106 (FIG. 2A). Highly similar sequences are also present upstream from the coding sequences of chitosanase genes found in other genomes of actinomycetes, displaying a clear consensus (FIG. 2B). Previous gel retardation experiments have shown an interaction between a protein present in partially purified cell extract from Kitasatospora sp. N106 and a short DNA segment including the palindromic sequence (Dubeau et al., 2005). Competition tests with mutated oligonucleotides allowed determining the bases which were critical for the interaction with the regulatory protein in vitro (FIG. 2B) (Dubeau et al., 2005). Two most important base pairs in the right half of the palindromic sequence were mutated (while keeping intact the original −10 and −35 promoter boxes) and introduced upstream from the csnN106 coding sequence, resulting in a third version of this heterologous gene. These three genes were introduced in two hosts: Streptomyces lividans TK24 (the host used so far in most works involving actinobacterial chitosanase studies) and a mutant harbouring an in-frame deletion in csnR gene (ΔcsnR, formerly described as Δ2657 h by Dubeau et al. 2007). The csnR gene (SSPG_04872, according to GenBank annotation) is coding for a putative transcriptional regulator of the endogenous chitosanase gene a protein belonging to the ROK family created by Titgemeyer et al. (1994).

Figure 3:
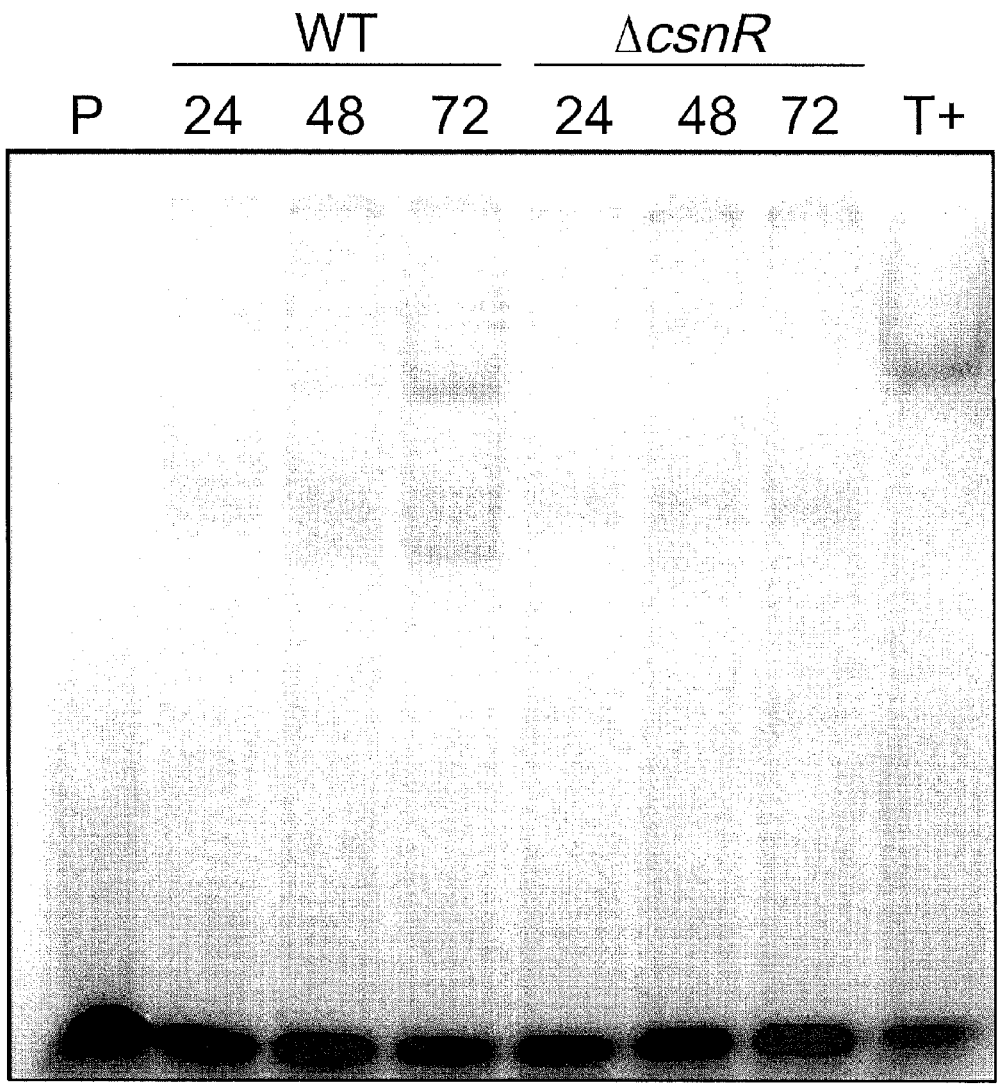
FIG. 3. Effect of csnR deletion on DNA-protein interaction at the csnN106 gene operator. Gel retardation experiment was set up combining 0.1 nM double strand oligonucleotide probe covering the palindromic box of csnN106 with 10 μg of crude protein extracts from *S. lividans* TK24 strain (WT) or the csnR deleted strain (ΔcsnR) cultivated in medium with 0.125% GlcN and 0.375% chitosan oligomers for the time (hours) indicated. P: probe only; T+: control reaction with 2 μg of partially purified protein from *Kitasatospora* sp. N106 (Dubeau et al., 2005).

Crude extracts prepared from the cells of both strains cultivated in the presence of chitosan oligosaccharides (a mixture of GlcN and chitosan oligomer) were used in gel retardation experiments using a $^{32}$P-labelled oligonucleotide including the palindromic sequence from csnN106 as a probe. A shift in mobility was observed with the extract from the wild type strain but not with ΔcsnR mutant (FIG. 3). The CsnR protein from S. lividans binds then efficiently the palindromic sequence of the heterologous csnN106 gene.

Chitosanase Production in the Absence of Chitosan or Derivatives.

In previous work, efficient production of chitosanase by either native or recombinant actinobacterial strains was strictly dependent on the addition of chitosan or derivatives (GlcN or chitooligosaccharides) in the culture media. Testing various concentrations of malt extract, salt formulations and methods of inoculation allowed obtaining routinely activities in the range of 10-12 units per ml and, in the best case, up to 24 units per ml. Protease activity was also highly dependent on medium composition and type of inoculum. Addition of magnesium ions was found to be important to promote efficient chitosanase production (and low level of protease), while the microelements of the M14 M medium could be omitted.

Figure 4A:
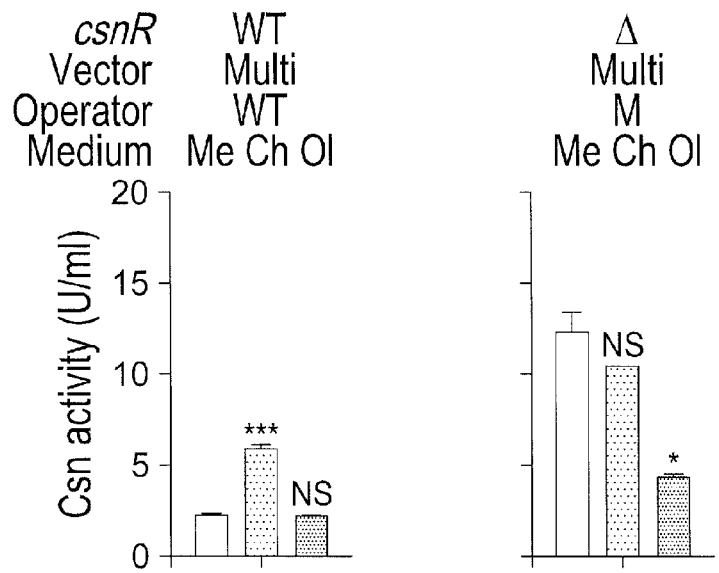
FIG. 4. Chitosanase activity and relative purity assessment and assay of protease levels. (A) chitosanase activity; (B) protease activity; (C) SDS-PAGE of proteins in culture supernatants. The upper table aligns the genotype of each strain and lists the type of medium for the corresponding columns in graphs (A) and (B) and wells of (C). WT=wild type; Δ=ΔcsnR mutant host; M=mutated palindromic box; Multi=chitosanase genes introduced on a multi-copy vector. Culture media: Me=malt extract medium; Ch=chitosan flakes medium; Ol=medium with GlcN and chitosan oligomers. All determinations have been done after 72 h of culture. Data and error bars (A and B) are the mean of culture duplicates. * $P \leq 0.001$,  $P \leq 0.01$, * $P \leq 0.05$ from one-way ANOVA with Bonferroni's post test (GraphPad Prism™ version 5.00). (C) 20 µl of culture supernatants were loaded on a 12% SDS-PAGE gel. PageRuler™ prestained protein ladder (0.5 µl; Fermentas) was used as standard. After electrophoresis, proteins were stained with Coomassie brilliant blue. Chitosanase migrates as a 26.5 kDa band.
Figure 4B:
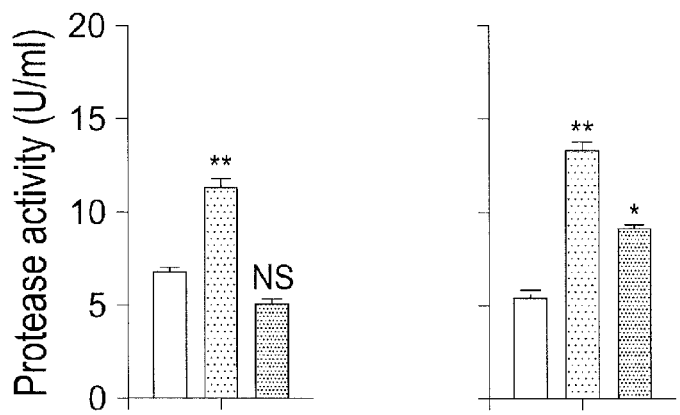
Figure 4C:
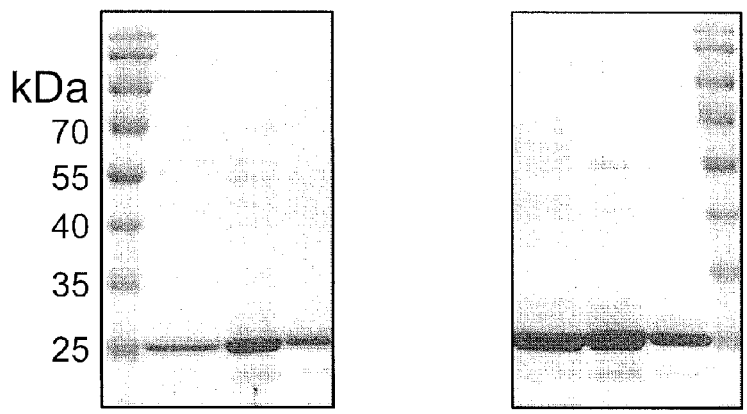

In previous work, chitosanase production was performed with S. lividans TK24 harbouring can genes originating from various bacterial species cloned in multicopy plasmids. To compare the new gene/host combination with the former ones, we cloned the csnN106 gene (with a wild type operator) into the multicopy vector pFDES and introduced it in the wild type host. In parallel, the same plasmid but with the mutated operator has been introduced into the ΔcsnR host. Chitosanase production by these two strains has been measured. Three media formulations were tested: a medium containing malt extract as main nutrient source, a medium with chitosan flakes and GlcN, often used in previous work, and a medium with more expensive components, GlcN and chitosan oligomers, used in basic research for the induction of chitosanase gene expression. On FIG. 4, only the 72 h time point is presented, as chitosanase level was maximal around this time point and then remained stable or slightly decreased. The culture in medium with chitosan flakes and GlcN gives the best chitosanase level for the strain keeping intact both partners of the regulatory interaction (FIG. 4A). However, cultures in media with chitosan gave much higher levels of extracellular proteases (FIG. 4B). Furthermore, the analysis of total extracellular proteins by SDS-PAGE revealed that there were less contaminant proteins in the malt extract medium than in the chitosan flakes medium (FIG. 4C). The ΔcsnR host seems to be particularly useful for the inexpensive production of almost pure chitosanase in stable, low-protease conditions.

Discussion

The results presented herein are dedicated to the genetic regulation of a heterologous chitosanase gene in S. lividans. It was shown that CsnR regulates negatively the expression of csnN106 gene. Deletion of csnR or mutations in the operator sequence of csnN106 resulted in the derepression of expression in the absence of inducer molecules. However, even in the derepressed gene/host combination, some residual induction by chitosan derivatives was still observed. This could be due to a regulator responding directly to the presence of chitosan or indirectly, through a stress pathway resulting from the interaction between chitosan and the cell. A complex transcriptomic response has been observed after contact with chitosan in cells of *Staphylococcus aureus* and *Saccharomyces cerevisiae*. One usual way to change the genetic regulation of a given gene is done by promoter replacement. In our earlier work, testing three different promoters from *Streptomycetes* did not led to the improvement of chitosanase production. As shown herein, the −35 and −10 boxes from csnN106 promoter sequence were replaced while conserving all the remaining segments. Despite the use of a promoter considered as strong, this substitution did not result in better chitosanase production. For reasons that remain unclear, the chitosanase expression was less efficient for a total of four different hybrid gene constructions when the protein coding sequence of Csn was separated from its native upstream segment. This could result from a lower stability of mRNAs transcribed from these hybrid genes, but this remains to be investigated. Masson et al. (1993) optimized a chitosanase production medium for the CsnN174 production in the heterologous host *S. lividans*.

Masson showed that the addition of malt extract to the chitosan medium was beneficial for enzyme production. The media formulations were based on malt extract in an attempt to produce chitosanase with the new gene/host combination in the absence of chitosan. It was shown that equivalent, and sometimes higher chitosanase levels can be obtained without the addition of chitosan to the culture medium. Interestingly, the new medium/host combination resulted in much lower levels of contaminant proteins in the supernatant. Finally, in earlier culture media formulations including chitosan flakes, a raise of extracellular protease activity at later culture stage could often result in a rapid loss of chitosanase activity (Masson et al., 1993). The new medium/host combination provides a substantial improvement, as protease levels are much lower, resulting in stable chitosanase production.

The chitosanase production system based on a new medium/host combination was shown to be at least as efficient as the former one without the necessity to include chitosan or derivatives into the culture medium. Extensive optimization of culture parameters will probably lead to much higher chitosanase activities. For biotechnology, the new host will be of interest for large scale chitosanase production as only inexpensive media components can be used.

Example II

CSNR-K.-O. Cells for the Expression of Endogenous Chitosanase

A palindromic sequence is present in the intergenic region preceding the chitosanase gene csnA (SSPG_06922) of *Streptomyces lividans* TK24. This sequence was also found in front of putative chitosanase genes in several other actinomycetes' genomes and upstream genes encoding putative transcriptional regulators of the ROK family, including csnR (SSPG_04872) in *S. lividans*. The latter was examined as a possible transcriptional regulator (CsnR) of chitosanase gene expression. In vitro, purified CsnR bound strongly to the palindromic sequences of the csnA and csnR genes (equilibrium dissociation constant [KD]=0.032 and 0.040 nM, respectively). Binding was impaired in the presence of chitosan oligosaccharides and d-glucosamine, and chitosan dimer was found to be the best effector, as determined by an equilibrium competition experiment and 50% inhibitory concentration ($IC_{50}$) determination, while glucose, N-acetyl-glucosamine, and galactosamine had no effect. In vivo, comparison of the *S. lividans* wild type and ΔCsnR strains using β-lactamase reporter genes showed that CsnR represses the expression of csnA and of its own gene, which was confirmed by quantitative PCR (qPCR). CsnR is localized at the beginning of a gene cluster, possibly an operon, the organization of which is conserved through many actinomycete genomes. The CsnR-mediated chitosanase regulation mechanism seems to be widespread among actinomycetes.

Materials and Methods

Bacterial Strains, Media, and Culture Conditions.

*Escherichia coli* DH5α™ (Invitrogen) was used as the host for cloning and DNA propagation. The methylase-negative mutant *E. coli* strain ET12567, containing the nontransmissible pUZ8002 plasmid was used as the donor in intergeneric conjugation with the *S. lividans* recipient. BL21 *E. coli* was used for recombinant CsnR production. *E. coli* strains were grown on Luria-Bertani (LB) broth supplemented, when necessary, with 100 µg/ml ampicillin (Ap), 34 µg/ml chloramphenicol (Cm), 500 µg/ml hygromycin (Hm), 50 µg/ml kanamycin (Km), 100 µg/ml spectinomycin (Sm), or 12.5 µg/ml tetracycline (Tet). Standard methods were used for *E. coli* transformation, plasmid isolation, and DNA manipulation. *S. lividans* TK24 (Dubeau et al., 2009) and the isogenic *S. lividans* ΔcsnR strain (formerly the Δ2657h strain) (Kieser et al., 2000) were used as recipients for transformation or conjugation. They were also used in quantitative PCR (qPCR) assays, while *Streptomyces avermitilis* MA-4680 was used in reverse transcription (RT)-PCR experiments.

DNA transformation with *S. lividans* protoplasts, using a rapid small-scale procedure and R5 regeneration medium, was performed as described previously (Kieser et al., 2000). Hm-resistant colonies were selected after DNA transfer by addition of 5 mg Hm to 2.5 ml of soft agar overlay. Transformants were chosen following two subsequent cycles of purification on solid yeast-malt extract (YME) medium (27) with 250 µg/ml Hm. Intergeneric conjugation was done with *S. lividans* ΔcsnR spores following a known protocol (Kieser et al., 2000). Approximately $5\times10^7$ spores of the *S. lividans* ΔcsnR strain and $5\times10^7$ cells of *E. coli* ET12567(pUZ8002) carrying the appropriate plasmid were combined for conjugation. The mixed bacteria were spread on SLM3 agar plates supplemented with 10 mM $MgCl_2$. Plates were overlaid with 1 ml of sterile water, including 5 mg Sm and 0.5 mg nalidixic acid per plate. Exconjugants were purified on solid YME medium with 200 µg/ml Sm and 25 µg/ml nalidixic acid. Sporulation was obtained by heavy inoculation of plates with SLM3 agar medium. Spores were collected with glass beads and stored in 20% glycerol at −20° C.

Production and Purification of CsnR.

The coding sequence of csnR was PCR amplified from *S. lividans* genomic DNA with the primers EcoRI-csnR and XhoI-csnR (see Table 2). The PCR product was digested with EcoRI and XhoI and ligated into pGEX-6P-1 vector (GE Healthcare) digested with the same enzymes, generating pGEX-csnR. This plasmid was used to produce the recombinant CsnR tagged with glutathione S-transferase (GST) at the N-terminus. For protein expression, the plasmid was transformed into BL21 *E. coli*. Transformants were selected on LB agar medium with Ap, Cm, and Tet. For production of CsnR, the transformant was grown in 1.25 liters of LB medium with Ap, Cm, and Tet inoculated 1:20 with overnight culture. Cultures were grown at 37° C. until the optical density at 600 nm (OD600) reached 0.4 to 0.6. Then 0.1 mM IPTG (isopropyl-β-d-thiogalactopyranoside) was added, and cultures were further incubated for 4 h at room temperature with shaking. Bacteria were recovered by centrifugation, and pellets were kept frozen at −80° C. For protein extraction, pellets were thawed for 15 min on ice and suspended in a total volume of 250 ml of phosphate-buffered saline. Then 1 mg/ml lysozyme was added, and the suspension was incubated for 30 min on ice. The suspension was treated by sonication with six rounds of 10-s bursts at 45% amplitude (130 W, 20 kHz) (Vibra-Cell; Sonics and Materials, Inc.) separated by 10 s cooling periods on ice. The lysate was centrifuged for 20 min at 10,000×g at 4° C. The supernatant (soluble crude extract) was incubated for 1 h at room temperature with 2 mM ATP and 5 mM $MgCl_2$. All further steps were done at 4° C. with cold solutions and centrifugation steps of 1 min at 500×g. The total volume of soluble crude extract (250 ml) was mixed with 1 ml of a 50% suspension of glutathione Sepharose 4B, divided into 50-ml aliquots, and incubated for 1 h with slight agitation. The suspensions were centrifuged, and the supernatants were transferred for a second round of binding with fresh resin. Pelleted resin was washed four times with 1.4 ml of phosphate-buffered saline (PBS) and two times with cleavage buffer (50 mM Tris-Cl, 150 mM NaCl, 1 mM EDTA, 1 mM dl-dithiothreitol [DTT] [pH 7.0]). For each wash, pelleted resin was incubated 10 min with slight agitation and centrifuged. For each resin aliquot, 16 µl of a specific protease cocktail (GE Healthcare) and 400 µl of cleavage buffer were added to cleave the GST tag from CsnR. Suspensions were pooled and incubated for 4 h at 4° C. The suspension was centrifuged, and the supernatant was saved. The resin pellet was suspended in 600 µl of cleavage buffer, incubated for 10 min, and centrifuged. Both supernatants were pooled and divided into three fractions for size exclusion chromatography. Approximately 500 µl of partially purified CsnR was loaded onto a Superdex™ 200 10/300 GL column (GE Healthcare), with a mixture of 137 mM NaCl, 2.7 mM KCl, 10 mM $Na_2HPO_4$, 2 mM $KH_2PO_4$, 5% glycerol, 0.5% Tween 20, and 1 mM DTT (pH 7.4) as the elution buffer. After SDS-PAGE analysis, purified fractions were pooled, aliquoted, and frozen at −80° C. until use. Identification of the contaminant protein from *E. coli* was performed by the Proteomics platform of the Quebec Genomics Center, Québec, Canada.

DNase I Footprinting.

To obtain end-labeled DNA probes, 30 pmol of the downward primers DF-csnR and DF-csnA (see Table 2) was end labeled with $[\gamma\text{-}32P]$ATP (3,000 Ci/mmol) (PerkinElmer) and 20 U of T4 polynucleotide kinase and then purified on a G-25 column (GE Healthcare). Approximately 20 pmol of the end-labeled primers was used in 50-µl PCRs. For csnR, pMP302-Δ2657h (Dubeau et al., 2009) was used as the template with the XbaI-csnRC primer. For csnA, pFDES-csnA was used as the template with UF-csnA primer. The end-labeled probes from PCR products were purified with the High Pure™ PCR product purification kit (Roche). DNA binding reaction mixtures (100 µl) contained 20 mM potassium phosphate buffer (pH 6.8), 5 mM $MgCl_2$, 150 mM KCl, 1 mM β-mercaptoethanol, 20% glycerol, 0.5 µg poly(dI-dC), approximately 20,000 cpm of end-labeled DNA probe, and ~0.5 nmol of purified CsnR. After 20 min of incubation at room temperature, 30 U of DNase I (Roche) was added to the reaction mixtures. After 90 s (60 s for reactions without protein), reactions were stopped by addition of 15 mM EDTA (pH 7.9). DNA fragments were extracted by phenol-chloroform and precipitated with 0.1 µg/µl yeast tRNA, 0.3 M sodium acetate (pH 5.2), and 2 volumes of isopropanol. Precipitated DNA was washed once with 70% ethanol, dried, and suspended in formamide loading buffer. Sequence reactions were done with end-labeled primers and DNA templates used in PCRs for probe labeling, and the ALFexpress AutoCycle™ sequencing kit (Amersham Biosciences) according to the manufacturer's recommendations. Samples and sequence reaction mixtures were heated for 5 min at 95° C. just before being loaded onto a 6% polyacrylamide sequencing gel. The gel was run, dried, visualized, and analyzed by a PhosphorImager™ with ImageQuant™ version 5.2 software (Molecular Dynamics).

EMSA.

For the electrophoretic mobility shift assay (EMSA), pairs of complementary oligonucleotides were annealed, generating double-stranded oligonucleotides csnA-WT (wild type), csnA-M1, csnA-M2, csnA-MM, and csnR-WT (see Table 3).

TABLE 2

PCR primers used in this example

| Aim of primers | Name | Sequence (5'→3') | SEQ ID NO: |
|---|---|---|---|
| For GST-CsnR production | EcoRI-csnR | GCGGTC<u>GAATTC</u>CAGGTGTGGACA | 26 |
|  | XhoI-csnR | ATTCCGGGC<u>CTCGAG</u>AAGCTCC | 27 |
| In DNase I footprinting | DF-csnR | CCTGCCATGCGTGTCCA | 28 |
|  | DF-csnA | CGGAAGGGGTGCCTCAC | 29 |
|  | UF-csnA | ACAACTTCGTCGCGCACATCCA | 30 |
| For IR-csnA cloning | BamHI-IR-csnA | GGAGCAGCC<u>GGATCC</u>CTGACGGA | 31 |
|  | SphI-IR-csnA | AGGGGTGCC<u>GCATGC</u>AATCTCCA | 32 |
| For IR-csnR cloning | BamHI-IR-csnR | GCACCAGCAA<u>GGATCC</u>CCGCCCG | 33 |
|  | SphI-IR-csnR | TGCGTGTCC<u>GCATGC</u>GCCTCTCG | 34 |
| For PCR-directed mutagenesis for IR-csnAMM cloning | Fw1-csnAMM | AATACGACACCAGATGGACGGC | 35 |
|  | Rv1-csnAMM | CCGGGCACTGAT<u>C</u>GGA<u>C</u>AGTTTC | 36 |
|  | Fw2-csnAMM | GAAACT<u>G</u>TCC<u>G</u>ATCAGTGCCGG | 37 |
|  | Rv2-csnAMM | TTGTCCTCCACCTTCCAGTCCTT | 38 |
| In complementation and DNAse I footprinting | XbaI-csnRC | TCCGCCG<u>TCTAGA</u>ACCAGCAA | 39 |
| In complementation | EcoRI-csnRC | CGAGGGCCG<u>GAATTC</u>TGGATAT | 40 |

Underlined bases pairs in oligonucleotide sequence correspond to restriction sites or mutated bases pairs from original sequence.

Fifty picomoles of double-stranded oligonucleotide was end labeled with [γ-32P]ATP (3,000 Ci/mmol) and 20 U of T4 polynucleotide kinase and purified on a G-25 column. DNA binding reaction mixtures (24 µl) contained 10 mM HEPES (pH 7.9), 10% glycerol, 0.2 mM EDTA, 0.5 mM phenylmethylsulfonyl fluoride (PMSF), 0.25 mM DTT, 1 µg poly(dI-dC), and 150 mM KCl. For equilibrium dissociation constant (KD) determination, various concentrations of labeled csnA-WT or csnR-WT probe (0.1 nM to 1.5 nM) and ~8.5 pmol of purified CsnR were used. For the determination of the 50% inhibitory concentration ($IC_{50}$) of the DNA competitors, 0.03 nM labeled csnA-WT probe and ~8.5 pmol of CsnR were used with various concentrations of competitor double-stranded oligonucleotide (0.1 to 125 nM). For the sugar binding assay, ~8.5 pmol of CsnR was preincubated with glucose, GlcNAc, galactosamine, GlcN, or chitosan oligosaccharides $(GlcN)_2$ to $(GlcN)_5$ at various concentrations (0.00075 to 75 mM) in the binding reaction mixture for 15 min on ice before the addition of labeled csnA-WT probe (0.03 nM). Reaction mixtures were incubated at room temperature for 15 min with the labeled probe and then subjected to electrophoresis at 4° C. in a prerun gel (15 min) of 6% polyacrylamide (10 mM Tris, 80 mM glycine, 0.4 mM EDTA [pH 8.3]). Following electrophoresis, gels were dried, and band intensities were visualized with a PhosphorImager™ and estimated with ImageQuant™ software (version 5.2). All determinations were done in triplicate. $K_D$ calculations were done with the Michaelis-Menten nonlinear fit (least squares), and the one-site log $IC_{50}$ nonlinear fit (least squares) was used for $IC_{50}$ calculations (GraphPad Prism™ version 5.03 for Windows; GraphPad, San Diego, Calif.).

TABLE 3

Double-stranded oligonucleotides used as probe or competitor DNA in EMSA experiments

| Name | Sequence (5'→3') | SEQ ID NO: |
|---|---|---|
| csnR-WT | CTCCAGCCAACAGGAAACTTTCCTAACAGA | 41 |
| csnA-WT | CCTCTTCTGGTAGGAAACTTTCCTATCAGT | 42 |
| csnA-M1 | CCTCTTCTGGTAGGAAACTGTCCTATCAGT | 43 |
| csnA-M2 | CCTCTTCTGGTAGGAAACTTTCCGATCAGT | 44 |
| csnA-MM | CCTCTTCTGGTAGGAAACTGTCCGATCAGT | 45 |

Genetic Complementation of the *S. lividans* ΔcsnR Strain.

The csnR gene coding sequence together with its complete upstream (211-bp) and downstream (106-bp) intergenic regions were PCR amplified from genomic DNA of *S. lividans* TK24 with primers XbaI-csnRC and EcoRI-csnRC (see Table 2). The PCR product was digested and introduced between the XbaI and EcoRI restriction sites of the integrative, conjugative vector pSET152m (Laing et al., 2006), generating pSETmC. Complementation plasmid was introduced into the *S. lividans* ΔcsnR strain by intergeneric conjugation. pSET152m vector was used as a negative control. Successful integration of vectors was confirmed by PCR analysis.

qPCR and Endpoint RT-PCR.

For quantitative PCR (qPCR) analysis, $2 \times 10^8$ spores of the *S. lividans* TK24, ΔcsnR, ΔcsnR+pSETmC, or ΔcsnR+pSET152m strain were inoculated into 50 ml TSB medium. The cultures were incubated at 30° C. for approximately 64 h with shaking. The cultures were centrifuged and then washed with sterile 0.9% saline, and the pellets were suspended in 2 volumes of saline. A total of 1.5 ml of this suspension was used to inoculate 50 ml of M14M (see above) either with mannitol or with 1:3 GlcN-chitosan oligomers. The experiment was done in triplicate. Cultures were incubated at 30° C. with shaking. After 14 h, 10 ml of each culture were collected and mixed immediately with stop solution (0.2 volume of 95:5 ethanol-phenol). Samples were centrifuged for 10 min at 4° C. Bacterial pellets were frozen at −80° C. until lysis. For RT-PCR experiments, culture conditions were identical to those for qRT-PCR experiments, except that *S. avermitilis* MA-4680 was grown for 24 h in M14M supplemented with 1% mannitol or 0.2% GlcN and 0.8% chitosan oligomers.

For qPCR and RT-PCR experiments, total RNA extraction was carried out with the Qiagen RNeasy™ minikit (Qiagen), with the following modifications. Cell disruption was achieved by sonication with two 30-s bursts at 35% amplitude separated by a 15-s cooling period. Sonication was followed by two phenol-chloroform extractions and one chloroform extraction for elimination of cell debris. The on-column DNase treatment was done with the RNase-free DNase set (Qiagen). Additionally, another DNase digestion was done after RNA elution with the Turbo DNA-free™ kit (Ambion). RNA purity and concentration were assessed in a NanoDrop™ 1000 spectrophotometer (Thermo Scientific). RNA quality was verified by electrophoresis on agarose gel in MOPS (morpholinepropanesulfonic acid) electrophoresis buffer with 0.22 M formaldehyde. Reverse transcription was performed on 2 µg of total RNA with the first-strand cDNA synthesis kit (GE Healthcare) and 72% G+C-rich random hexamers.

Quantitative PCRs were performed in an Mx3000P™ real-time PCR system (Stratagene). PCR mixtures (20 µl) contained 2 µl of 20× diluted template cDNA, 250 nM the appropriate primer (see Table 4), and a SYBR™ green PCR mix. The PCR conditions were 95° C. for 3 min, followed by 40 cycles at 95° C. for 15 s, 60° C. for 45 s, and 72° C. for 15 s. An additional dissociation step (95° C. for 1 min, 60° C. for 30 s, and 95° C. for 30 s) was added to assess nonspecific amplification. PCRs were run in triplicate. The absence of genomic DNA was verified by using samples in which the reverse transcriptase was omitted from the cDNA synthesis reaction. The gyrA and rrn genes of *S. lividans* (encoding gyrase A and 16S rRNA, respectively) were used as internal controls for relative quantification. Efficiencies of all primer pairs were verified. Raw data were transformed into threshold cycle (CT) values. Relative gene expression was calculated by the comparative CT method (Pfaffl et al., 2001) for each strain incubated in the GlcN-chitosan oligomer medium compared to the mannitol medium.

TABLE 4

Set of primers used for qRT-PCR experiments

| Gene symbol/ annotation | Primer sequence (5'→3') | Expected fragment size (bp) | SEQ ID NO: |
|---|---|---|---|
| csnA | ACCGGTACATCGAGGACATCGG | 139 | 46 |
|  | AGATAGGGCGCGAGGACGTT |  | 47 |
| csnR | GGTCGAGTACGAGAACGACGTGAA | 96 | 48 |
|  | TGGTTCCACAGCAGGACGAAGT |  | 49 |
| csnE | GAACTACCACGGCTACGAGACC | 182 | 50 |
|  | TGTTGCGGTACTTCTCCAGCTTCT |  | 51 |
| csnH | CCTCCTACTACCTGCGCTACTACT | 112 | 52 |
|  | ATCTGCAGCAGTTGCCGTTCCAT |  | 53 |

TABLE 4-continued

Set of primers used for qRT-PCR experiments

| Gene symbol/ annotation | Primer sequence (5'→3') | Expected fragment size (bp) | SEQ ID NO: |
|---|---|---|---|
| csnB | GCCGAGAACTCGACCACGAAGT | 136 | 54 |
| | TGTAGCGCTCGACCAGCATGA | | 55 |
| SPPG_04866 | ACCACCATCGCGAAGCTCAA | 139 | 56 |
| | GCATCTCCTTCTGCATCTTCTCGT | | 57 |
| gyrA | GCGACGACCGCAAGACCAAGCTGAT | 84 | 58 |
| | TGACGACGATGTCCTCCTCGGCGAT | | 59 |
| rrn | TCTGGGCCGATACTGACGCTGAGGA | 105 | 60 |
| | ATGTTGCCCACACCTAGTGCCCACC | | 61 |

For RT-PCR experiments with S. avermitilis MA-480, an endpoint PCR followed reverse transcription reactions. PCR mixtures (20 μl) contained 1 μl of 10× diluted template of cDNA, 2 μM each primer (see Table 5), 10% dimethyl sulfoxide (DMSO), 1× ThermoPol buffer, and 250 μM deoxynucleoside triphosphates (dNTPs). The PCR conditions were 95° C. for 3 min, followed by 35 cycles at 95° C. for 30 s, 58.5 to 66.4° C. (depending on the set of primers used) and 72° C. for 30 s, with a final elongation step at 72° for 10 min. The rps1 gene of S. avermitilis (encoding the 30S ribosomal protein S9) was used as an internal control.

TABLE 5

Sets of primers used for PCRs in the RT-PCR experiment.

| Gene symbol/ annotation | Primer sequence (5'→3') | Expected fragment size (bp) | SEQ ID NO: |
|---|---|---|---|
| SAV_1223 | TTCCAGGTGCCGTGGTGGTA | 266 | 62 |
| | AGCCAGTCGATCCAGCCCAT | | 63 |
| SAV_2015 | CACCAGCTTCAGCAGCATCCG | 245 | 64 |
| | AGCCGATGTGGTAGCTGTCCC | | 65 |
| SAV_6191 | GCCATGAAACGTGCCGCTCT | 229 | 66 |
| | GCCAGTCCAGGGTGGAGTTCT | | 67 |
| SAV_1288 | AATGCCGAGACCCTGCCGTA | 284 | 68 |
| | ACGTGGTTCTCGATGGGCGA | | 69 |
| SAV_1850 | TTCCACCAGTCCGACGGCAA | 299 | 70 |
| | ATGGGCGAGACCTGCGAGTT | | 71 |
| rps1 | GCAGGAAGTCAACGAGCCCTTC | 290 | 72 |
| | CTTGCTGTACTGCGGGGCCTT | | 73 |

Results

Identification of a candidate gene regulating chitosanase expression. Palindromic sequences of similar lengths and sharing a high level of identity have been previously described in the upstream segments of several endo- and exochitosanase genes from actinomycetes. By EMSA experiments, a DNA-protein interaction between a protein present in partially purified extracts from Kitasatospora sp. N106 and a double-stranded oligonucleotide probe covering the palindromic sequence was characterized. A BLAST search with this sequence as the query returned numerous hits, mostly from intergenic regions of actinomycete genomes. Their partial listing was used in an alignment (FIG. 5) and yielded the following consensus:

(SEQ ID NO: 88)
[AC][AC][AC][CT][TGC][GA][TA]TAGGAAA[CG]TTTCCTAAC
[AT][GA][AT]

The palindromic sequence was found in front of two categories of genes: those encoding studied or putative chitosanases from various families (including the csnA gene, SSPG_06922, from S. lividans) and genes encoding putative transcriptional regulators, all belonging to the ROK family established by Titgemeyer et al. (1994): among these are S. lividans gene SSPG_04872, localized at map coordinate 5.42 Mb at a 2.2-Mb distance from csnA. The protein encoded by this gene as a possible candidate for a transcriptional regulator of chitosanase gene expression (CsnR) was examined.

Purification of CsnR. CsnR was overproduced with a GST tag. The majority of the recombinant protein was detected in inclusion bodies. Attempts to renaturate the insoluble protein were not successful as precipitation during dialysis occurred. Purification was then attempted with the soluble portion of the lysate. A major protein contaminant (~60 kDa) copurified with GST-CsnR (FIG. 6). This protein was identified by partial sequencing as the chaperone GroEL, known to contaminate several recombinant proteins from E. coli during purification. The soluble lysate was incubated with 2 mM ATP and 5 mM MgCl$_2$ before the affinity purification step. This additional step was helpful in eliminating the contaminant (FIG. 6). After an additional size exclusion chromatography step, essentially pure CsnR was obtained, as shown by SDS-PAGE followed by silver nitrate staining (FIG. 6).

CsnR Binds In Vitro to the Palindromic Sequences Upstream of csnA and csnR.

As determined by DNase I footprinting, CsnR binds asymmetrically to the palindromic box found in the promoter region of csnA, covering 15 nucleotides upstream and 12 nucleotides downstream from the palindrome axis (FIG. 7). CsnR binds in a similar way to the palindromic box in the promoter region of its own gene, covering 17 nucleotides upstream and 12 nucleotides downstream from the axis (FIG. 7). As determined by primer extension, the protected region superimposes to the transcriptional start site in csnR gene (FIG. 7B). Despite several attempts, the transcription start site of csnA could not be determined.

Figure 8:
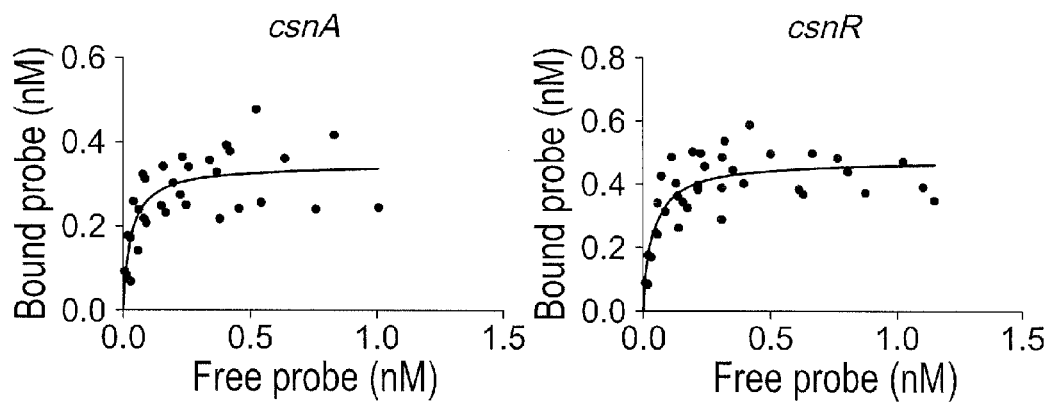
FIG. 8. Determination of dissociation constant (KD). Various concentrations of labeled csnA-WT or csnR-WT probe (0.1 nM to 1.5 nM) and 1 µl of purified CsnR were used in electrophoretic mobility shift reactions. Data were collected from bands intensities analysis using ImageQuant™ software (version 5.2). KD calculations were done using the Michaelis-Menten non-linear fit (least squares) GraphPad Prism™ version 5.03 for Windows. For the csnA probe, the best-fit $K_D$ value was calculated to be 0.032 nM, the standard error to 0.009 nM and the $R^2$ to 0.63. For the csnR probe, the best-fit $K_D$ value was calculated to be 0.04 nM, the standard error to 0.008 nM and the $R^2$ to 0.75.

Oligonucleotide probes corresponding to the longest protected segment (17-1-12) were used to characterize the CsnR-DNA interaction by EMSA. The $K_D$ values were 0.032 nM (standard error [SE]=0.009) and 0.040 nM (SE=0.008) for the operators of csnA and csnR, respectively (see FIG. 8). It appears that CsnR binds to the operators of the chitosanase gene as well as its own gene with similar affinity.

On the basis of our previous experiments performed in vitro with partly purified protein extracts from Kitasatospora sp. N106 and mutated oligonucleotides representing the operator of the chitosanase N106 gene, it was hypothesized that nucleotides at the −2 and +2 positions were critical for binding, while positions −7, −6, +6, and +7 were of moderate importance. Accordingly, annealed double-stranded oligonucleotides corresponding to the CsnR target sequence mutated by transversion at positions +2 and/or +6 of the palindrome were used in equilibrium competition experiments against a labeled csnA-WT probe (Table 6). The effect of mutations on binding was estimated from $IC_{50}$s. The mutation at the +2 position was particularly deleterious for binding (Table 6). Mutation at the +6 position had a lesser effect, and the double mutation seemed to bring a cooperative effect. The doubly mutated oligonucleotide lost most of its affinity for the CsnR protein. This suggests a similarity between the DNA binding mechanism of CsnR from *S. lividans* and that of the putative chitosanase gene regulator from *Kitasatospora* sp. N106.

TABLE 6

Effect of mutations in the operator sequence on CsnR binding evaluated by equilibrium competition experiments

| Name | Sequence (5'→3') [a] -6  -2 0 + 2  +6 | $IC_{50}$ [b] (nM) | SE of $logIC_{50}$ [b] |
|---|---|---|---|
| csnA-WT | CCTCTTCTGGTAGGAAACTTTCCTATCAGT | 1.3 | 0.11 |
| csnA-M1 | CCTCTTCTGGTAGGAAACTGTCCTATCAGT | 52.1 | 0.13 |
| csnA-M2 | CCTCTTCTGGTAGGAAACTTTCCGATCAGT | 2.7 | 0.08 |
| csnA-MM | CCTCTTCTGGTAGGAAACTGTCCGATCAGT | 105 | 0.33 |

[a] Mutated nucleotides are in boldface.
[b] $IC_{50}$ and standard error of log $IC_{50}$ values were determined using Graph-Pad Prism software from data compilation of three independent experiments.

DNA Binding by CsnR is Sensitive to the Presence of Chitosan Oligomers.

Figure 9:
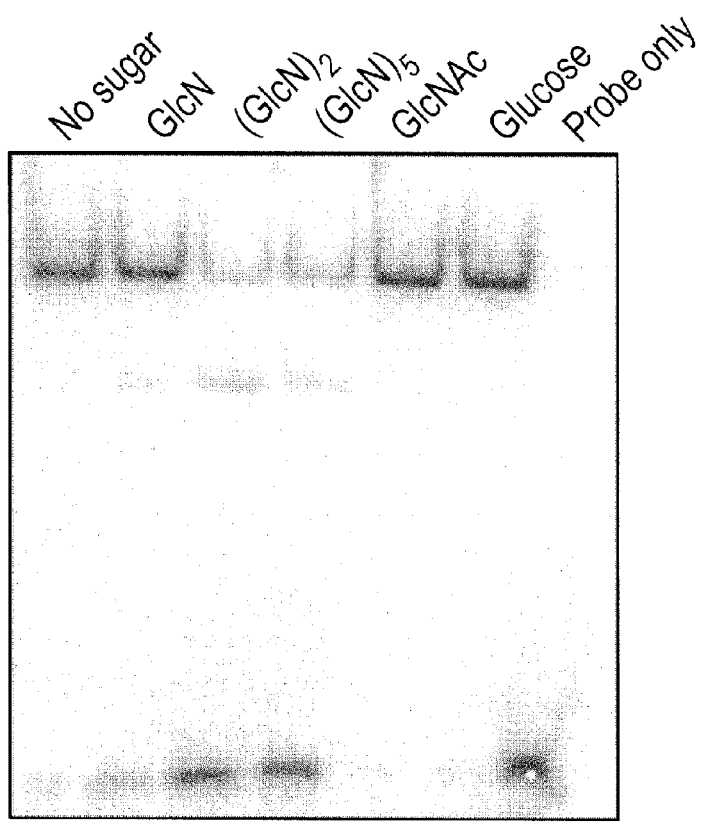
FIG. 9. Effect of saccharides on the interaction between CsnR and the csnA-WT operator. The indicated saccharides were added (500 nM) to binding reaction mixtures containing ~8.5 pmol of CsnR and 0.03 nM csnA-WT probe. Free and complexed DNA fragments were separated by 6% polyacrylamide gel electrophoresis and visualized by PhosphorImager™.
Figure 10:
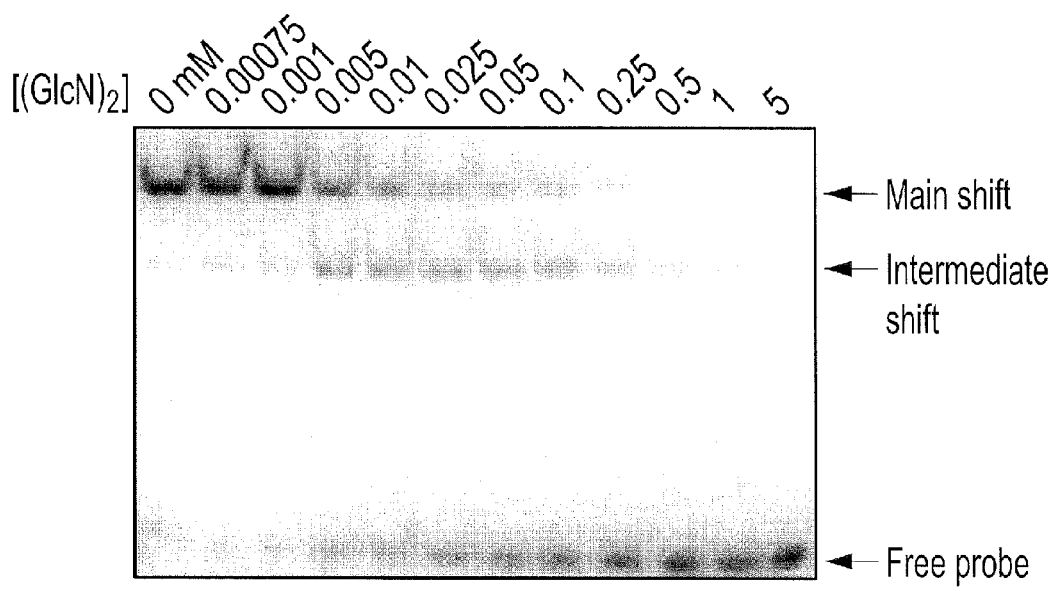
FIG. 10. Chitosan dimer $IC_{50}$ determination. Electrophoretic mobility shift reactions were done with ~8.5 pmol of CsnR, pre-incubated with $(GlcN)_2$ at various concentrations (0.00075 mM to 5 mM as indicated in the row above the figure) for 15 min on ice before the addition of labelled csnA-WT probe (0.03 nM). Two specific shifts were observed and considered in the $IC_{50}$ determination.

Equilibrium competition experiments were also used to determine the ability of various carbohydrates to interfere with DNA binding of CsnR to operator sequence of csnA. At first, EMSA experiments with CsnR showed that 500 nM GlcN, chitosan dimer, and chitosan pentamer strongly affected the gel shift pattern, while glucose and GlcNAc had no effect (FIG. 9). Then detailed $IC_{50}$ determinations revealed that the chitosan dimer had the strongest effect on the displacement of CsnR from its target, having the lowest $IC_{50}$ (18.2 nM; SE of log $IC_{50}$=0.05), compared to the chitosan monomer, GlcN (977 nM; SE of log $IC_{50}$=0.05). For higher oligomers, the $IC_{50}$ increased progressively with their length: 30.6 nM (SE of log $IC_{50}$=0.08) for trimer, 37.3 nM (SE of log $IC_{50}$=0.08) for tetramer, and 154 nM (SE of log $IC_{50}$=0.080) for pentamer. CsnR seems to bind specifically the products of chitosan degradation by chitosanases, as the other tested sugars (glucose, galactosamine, and GlcNAc) do not interfere with CsnR binding to the csnA-WT probe even at the maximal tested concentration of 75 mM in binding reactions. When undersaturating concentrations of chitosan oligosaccharides were present in the binding reaction mixtures, a band of intermediate mobility appeared in EMSA gels (FIG. 9 and see FIG. 10), reflecting the progressive disassembly of the multimeric complex of CsnR with its DNA target.

CsnR Regulates Negatively the Transcription of csnA and of a Gene Cluster LED by csnR.

Figure 11:
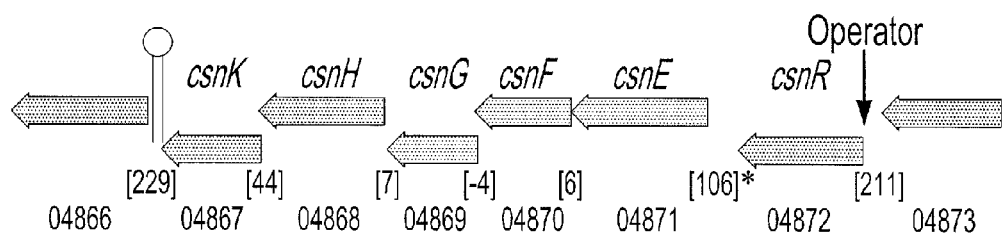
FIG. 11. *S. lividans* TK24 gene cluster led by csnR. Black arrows cover the coding sequence of each gene and are numbered according to the annotation in *S. lividans* genome. Gene symbols attributed in this study are shown in italics. The vertical arrow shows the position of CsnR palindromic operator. The stem-loop indicates the position of a putative transcriptional terminator. The length of each intergenic segment is given in brackets. (*) indicates segment sequenced in the current work.

Close examination of the genomic sequence of *S. lividans* reveals that csnR is localized in a gene cluster composed of six genes (Table 7 and see FIG. 11). The functions putatively assigned to these genes indicate that the cluster could be dedicated to sugar transport and metabolism (Table 7). The intergenic regions between these genes are very short (the longest region of 106 bp being localized between csnR and csnE), while a much larger region containing a possible transcription terminator consisting of a 14-bp inverted repeat, separates csnK from the following gene, SSPG_04866 (see FIG. 11).

TABLE 7

Components of csnR-led gene cluster in *S. lividans*.

| Gene annotation | Gene symbol | Putative function |
|---|---|---|
| SSPG_04872 | csnR | ROK-family transcriptional regulator |
| SSPG_04871* | csnE | Secreted sugar binding protein |

TABLE 7-continued

Components of csnR-led gene cluster in *S. lividans*.

| Gene annotation | Gene symbol | Putative function |
|---|---|---|
| SSPG_04870* | csnF | Sugar transport system permease |
| SSPG_04869* | csnG | Sugar transport membrane protein |
| SSPG_04868 | csnH | Glycoside hydrolase, family GH4 |
| SSPG_04867 | csnK | Sugar kinase |

[a] Names were adopted as described by Bertram et al. (2004).
[b] These three genes determine a putative ABC transporter.

To get more insight into the regulatory mechanism of CsnR, the transcript abundance of various genes was evaluated by qPCR in both wild-type and ΔcsnR strains (Table 8). A mutant strain in which the deletion has been complemented by a wild-type copy of the csnR gene (including its entire 211-bp upstream IR) on an integrative vector (*S. lividans* ΔcsnR+pSETmC) was examined (Table 8). Data were collected from cultures growing in control medium with mannitol or in M14M with chitosan-derived carbon sources. There was no detectable csnR expression in either the ΔcsnR strain or the control complementation strain (*S. lividans* ΔcsnR+pSET152m strain), confirming the deletion genotype. It was found that the expression of csnR itself was induced more than 100× by chitosan-derived saccharides (Table 8), but, surprisingly, the induction ratio was very low in the complementation strain when csnR was introduced in a different genomic location with the integrative plasmid pSETmC. This appeared to be due to unexpectedly high csnR transcript abundance in the mannitol medium (Table 8). In other words, CsnR failed to autorepress transcription when its own gene (including its operator) was carried by the integrated pSETmC vector.

TABLE 8

Effect of the ΔcsnR mutation and its complementation on transcript abundance patterns of chitosan-related genes in *S. lividans* strains. Results are shown as mean ± SE relative abundance and induction ratio[a]

| S. lividans strains | | csnA M ± SE | csnB M ± SE | csnR M ± SE | csnE M ± SE | csnH M ± SE | SSPG_04866 M ± SE |
|---|---|---|---|---|---|---|---|
| TK24 | C[a] | 0.096 ± 0.0032 | 0.023 ± 0.0017 | 0.0055 ± 0.0022 | 0.0011 ± 0.000033 | 0.26 ± 0.0029 | 0.097 ± 0.0049 |
| | I[a] | 4.2 ± 0.67 | 0.070 ± 0.0054 | 0.86 ± 0.35 | 1.6 ± 0.36 | 2.0 ± 0.23 | 0.35 ± 0.063 |
| | R[b] | 43 | 3.0 | 156 | 1398 | 78 | 3.6 |
| ΔcsnR | C | 9.4 ± 0.86 | 0.16 ± 0.019 | ND | 1.5 ± 0.17 | 1.5 ± 0.14 | 0.58 ± 0.079 |
| | I | 7.0 ± 0.51 | 0.30 ± 0.022 | | 2.3 ± 0.39 | 2.4 ± 0.26 | 0.60 ± 0.020 |
| | R | 0.74 | 1.9 | | 1.5 | 1.7 | 1.0 |
| ΔcsnR + pSETmC | C | 0.13 ± 0.0073 | 0.034 ± 0.0068 | 0.14 ± 0.018 | 0.0016 ± 0.000088 | 0.025 ± 0.0022 | 0.15 ± 0.023 |
| | I | 3.0 ± 0.29 | 0.054 ± 0.0046 | 0.42 ± 0.14 | 1.2 ± 0.20 | 2.5 ± 0.17 | 0.36 ± 0.048 |
| | R | 23 | 1.6 | 3.0 | 734 | 100 | 2.4 |
| ΔcsnR + pSET152m | C | 1.6 ± 0.26 | 0.067 ± 0.0050 | ND | 0.96 ± 0.089 | 2.0 ± 0.27 | 0.11 ± 0.019 |
| | I | 0.77 ± 0.15 | 0.026 ± 0.0041 | | 1.4 ± 0.077 | 2.8 ± 0.15 | 0.056 ± 0.017 |
| | R | 0.47 | 0.40 | | 1.4 | 1.4 | 0.51 |

[a]The values shown are expressed as the relative transcript abundance in the control medium or in induction medium normalized to the transcript abundance of the gyrA gene. Similar values were obtained after normalization to the expression level of rrn (data not shown). The values shown are means ± SEs of three independent cultures with a culture time of 14 h. Induction ratios represent the ratio of transcript abundance in the induction medium to that in control medium. ND, not determined.
[b]R (induction ratio) is the ratio of transcript abundance in the induction medium to that in control medium.

For the chitosanase gene, csnA, a 43-fold induction ratio was observed (Table 8). Complete derepression of csnA expression was observed in the ΔcsnR strain, and repression was restored by complementation (Table 8). A similar CsnR-dependent expression pattern was observed for genes csnE and csnH localized inside the cluster (Table 8). It is thus probable that this cluster forms a polycistronic transcription unit negatively regulated by CsnR.

A much higher induction ratio was however observed for csnE than for csnR and csnH (Table 8). The intergenic region between csnR and csnE was sequenced and it was observed that it includes four direct repeats (see FIG. 12), a possible site of a regulatory interaction.

Transcript abundance of SSPG_04866, the gene following csnK, did not follow a CsnR-dependent pattern (Table 8). SSPG_04866 putatively encodes a secreted protein of unknown function and does not seem to belong functionally to the csnR to -K gene cluster. An extensive inverted repeat localized in the IR following csnK could function as a transcription terminator (see FIG. 11).

While there is provided evidence that CsnR is the transcriptional repressor of the chitosanase gene csnA, the uniform expression pattern observed for its homolog, csnB (SSPG_05520), indicated that csnB is not regulated by CsnR (Table 8). This was somewhat expected, as the palindromic sequence recognized by CsnR was not found in the genomic environment of csnB.

The CsnR-Mediated Regulatory Mechanism is Widespread in Actinobacteria.

After the identification of the csnR to -K gene cluster in *S. lividans*, a bioinformatic search was performed to establish if similar gene clusters are present in other fully or partly assembled genomes. So far, orthologs of CsnR with no less than 46% identity have been found in 23 genomes of actinobacteria, and the presence of a highly similar gene cluster of six genes has been confirmed in 12 genomes, including actinobacteria other than *Streptomycetes*, such as *Saccharopolyspora erythraea* NRRL2338, *Streptosporangium roseum* DSM43021, and *Kribbella flavida* DSM17836. Table 9 shows the cluster annotation in some streptomycete species in which a palindromic box corresponding to the CsnR consensus presented in FIG. 5 is present upstream of the gene cluster. All the putative chitosanase genes belonging to well-established glycoside hydrolase (GH) families are also listed (Table 9). While the distributions of members of various GH families differ among the analyzed species, it is noteworthy that each genome includes at least one putative chitosanase gene provided with a CsnR box.

TABLE 9

CsnR gene clusters and putative chitosanase genes in sequenced *Streptomyces* genomes

| | CsnR cluster components[a] | | Confirmed[*] or putative exo and endo-chitosanase genes | | | |
|---|---|---|---|---|---|---|
| | | | GH2 | | GH5 | |
| Species and strain | CsnR | CsnK | Gene | Box | Gene | Box |
| *Streptomyces lividans* TK24 | SSPG_04872 | SSPG_04867 | | | | |
| *Streptomyces coelicolor* A3(2) | SCO2657 | SCO2662 | | | | |
| *Streptomyces avermitilis* MA-4680 | SAV_5384 | SAV_5379 | SAV_1223[*] | + | | |
| *Streptomyces scabies* 87.22 | SCAB_59491 | SCAB_59441 | | | SCAB_86311 | + |

TABLE 9-continued

CsnR gene clusters and putative chitosanase genes in sequenced *Streptomyces* genomes

| Species and strain | | | | | | |
|---|---|---|---|---|---|---|
| *Streptomyces griseus* IFO 13350 | SGR_4874 | SGR_4869 | | | SGR_1341(*) | + |
| *Streptomyces sviceus* ATCC 29083 | SSEG_04515: | SSEG_09503 (b) | | | | |
| *Streptomyces clavuligerus* ATCC 27064 | SCLAV_1826 | SCLAV_1831 | | | SCLAV_5580 | + |
| *Streptomyces pristinaespiralis* ATCC 25486 | SSDG_02817 | SSDG_02822 | | | SSDG_05015 | + |
| *Streptomyces hygroscopicus* subsp. *jinggangensis* 5008 | SHJG_4161 | SHJG_4166 | SHJG_2189 | + | | |
| *Streptomyces venezuelae* ATCC 10712 | SVEN_2441 | SVEN_2446 | | | SVEN_6970 | + |
| *Streptomyces violaceusniger* Tu 4113 | STRVI_7945 | STRVI_7950 | STRVI_3876 | | | |
| *Streptomyces cattleya* NRRL8057 | SCAT_1767 | SCAT_1771 | | | | |
| *Streptomyces flavogriseus* ATCC33331 | SFLA_4225 | SFLA_4220 | | | | |
| *Streptosporangium roseum* DSM43021 | SROS_5819 | SROS_5824 | | | | |

| | Confirmed(*) or putative exo and endo-chitosanase genes | | | | | |
|---|---|---|---|---|---|---|
| Species and strain | GH46 | | GH75 | | GH8 | |
| | Gene | Box | Gene | Box | Gene | Box |
| *Streptomyces lividans* TK24 | SSPG_06922(*) SSPG_05520 | + − | SSPG_00778 | − | | |
| *Streptomyces coelicolor* A3(2) | SCO0677(*) SCO2024 | + − | SCO7070 | − | | |
| *Streptomyces avermitilis* MA-4680 | SAV_2015 SAV_6191 | + − | SAV_1850(*) SAV_1288 | + − | | |
| *Streptomyces scabies* 87.22 | | | SCAB_83781 | − | | |
| *Streptomyces griseus* IFO 13350 | | | SGR_1238 | − | | |
| *Streptomyces sviceus* ATCC 29083 | SSEG_02093 SSEG_10482 | − + | SSEG_10562 | − | | |
| *Streptomyces clavuligerus* ATCC 27064 | SCLAV_4996 | − | SCLAV_5034 | − | | |
| *Streptomyces pristinaespiralis* ATCC 25486 | SSDG_00156 SSDG_03879 | − − | SSDG_04141 | − | | |
| *Streptomyces hygroscopicus* subsp. *jinggangensis* 5008 | SHJG_1996 | + | SHJG_7504 SHJG_2272 | + − | | |
| *Streptomyces venezuelae* ATCC 10712 | | | | | SVEN_6947 | + |
| *Streptomyces violaceusniger* Tu 4113 | STRVI_2888 | + | STRVI_3855 | + | STRVI_8945 | − |
| *Streptomyces cattleya* NRRL8057 | SCAT_5429 | + | | | | |

TABLE 9-continued

CsnR gene clusters and putative chitosanase genes in sequenced *Streptomyces* genomes

| | | | | |
|---|---|---|---|---|
| *Streptomyces flavogriseus* ATCC33331 | SFLA_1048 SFLA_1047 | + − | SFLA_0970 | − |
| *Streptosporangium roseum* DSM43021 | SROS_2053 | + | SROS_1551 | + |

Figure 13:
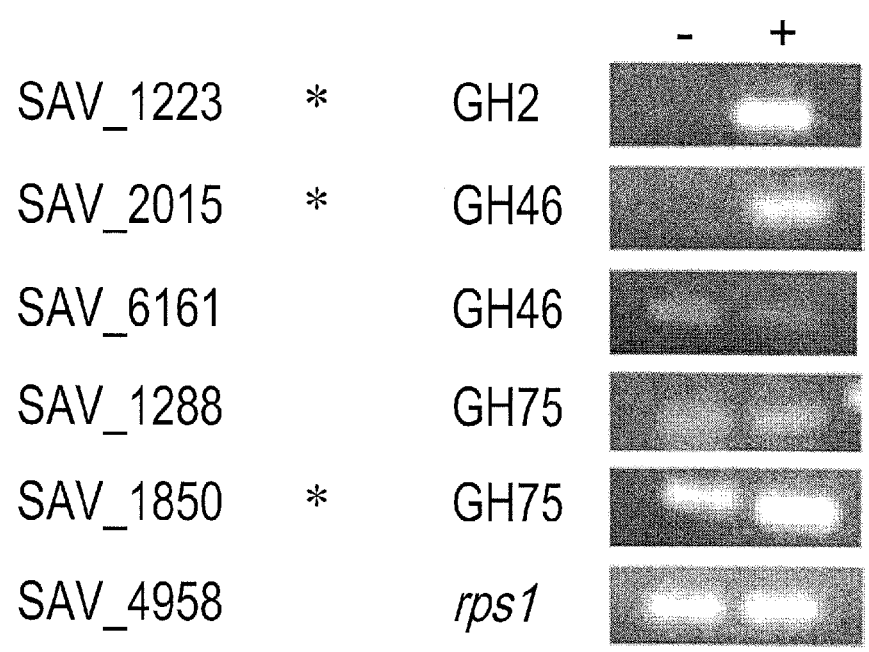
FIG. 13. RT-PCR expression profiling of putative chitosanase genes belonging to families GH2 (SAV_1223), GH46 (SAV_2015 and SAV_6161), and GH75 (SAV_1288 and SAV_1850) in *Streptomyces avermitilis* grown in the absence (−) or presence (+) of chitosan oligosaccharides. Expression of the SAV_4958 (rps1) gene was used as an internal control. Asterisks indicate chitosanase genes with the CsnR box.

[a] All clusters begin with a csnR ortholog having the palindromic box in the upstream segment
[b] This gene is localized in an uninterrupted cluster with CsnR even if their numbers are not closely related
[*] These genes encode enzymes which identity as chitosanases have been confirmed by biochemical studies Among the analyzed species, *S. avermitilis* stands out for its highest number of putative chitosanase genes, belonging to three different families. The transcriptional behavior of all these putative chitosanases in the absence or the presence of chitosan oligomers was thus compared by endpoint RT-PCR. Induction with chitosan-derived oligosaccharides was observed only for the three putative chitosanase genes having a CsnR-type operator (FIG. 13).

Our data indicate that the regulatory mechanism mediated by CsnR is an evolutionary ancient mechanism of chitosanase gene regulation present in many actinobacteria and not limited to the GH46 family in which it was discovered, but extends to other chitosanase families as well.

Discussion

It is herewith described the identification and characterization of CsnR, a novel chitosanase gene regulator in bacteria and also the first characterized transcriptional regulator of the ROK family in actinobacteria. DNase footprinting and EMSA experiments demonstrated that CsnR binds directly to the palindromic box found upstream from the csnA and csnR gene cluster. This binding target is different from the operators characterized for other transcriptional regulators belonging to the ROK family. The CsnR box is tightly organized around the symmetry axis, the positions −2 and +2 being most critical for binding. In contrast, the operator consensus sequences of NagC and Mlc of *E. coli* and XylR of Firmicutes are essentially composed of two A/T-rich inverted repeats separated by a 5- to 9-bp spacer with strictly conserved positions ±6 and ±5. Equilibrium competition experiments showed that $(GlcN)_2$ is the preferential CsnR ligand molecule. This dimer is the major product obtained from chitosan hydrolysis by endochitosanases. Oligosaccharide products resulting from the hydrolysis of polymers catalyzed by endohydrolases were often described as the effectors for the transcriptional regulation of glycoside hydrolase genes in actinomycetes. Cellopentaose is the inducer of CebR, the repressor of cell in *Streptomyces reticuli*. Maltopentaose is the inducer of MalR, the repressor of genes coding for α-amylase in *Streptomyces coelicolor* A3(2). Direct estimation of transcript abundance with qPCR (Table 8) showed that CsnR is subject to autorepression. It was previously showed that a system controlled by negative autoregulation offers the advantage of faster response to the presence of inducer molecules over a system controlled by an open loop regulator. Also, negative autoregulation ensures a more homogenous distribution of the steady-state level of the repressor between cells in a population. In *S. lividans*, *S. coelicolor* A3(2), and several other actinobacteria, CsnR is localized at the beginning of a gene cluster (csnREFGHK) including an ABC transporter, a glycoside hydrolase, and a sugar kinase. Previously, close orthologs of csnEFG in the *S. coelicolor* A3(2) genome (SCO2658 to SCO2660; localized on the SC6D10.01 cosmid) have been described and found by in silico analysis of carbohydrate uptake systems. Trehalose, maltose, and lactose were cited as possible substrates for this uptake system. Our study indicates that the transcription of genes localized in this cluster is induced by chitosan oligosaccharides and that they share a negative regulatory mechanism with the chitosanase gene, csnA. It is suggested that this cluster represents an operon-like structure involved in the uptake, transport and intracellular metabolism of oligosaccharides resulting from the hydrolysis of chitosan (or N-deacetylated segments of chitin) by chitosanases. As shown in Table 9, gene clusters highly similar to csnREFGHK of *S. lividans* were found in several other actinobacterial genomes.

Example III

Optimization of Chitosanase Production

Spores of *S. lividans* ΔcsnR strain harboring a heterologous chitosanase gene (as described in Example I) were inoculated into tryptic soy broth (ratio of $2 \times 10^9$ spores per 100 ml of broth) and incubated for 64 h at 30° C. with shaking (250 rpm) to obtain a dense pre-culture. A small volume (50 ml) of this pre-culture was centrifuged (10 min at 3000×g) in order to measure the pellet volume equivalents. This dense pre-culture was used to inoculate directly the chitosanase production medium in a ratio of four ml of pellet volume equivalents per 100 ml of chitosanase production medium. This culture was incubated (30° C., 300 rpm) for further 72-96 h. Chitosanase and protease activities as well as total protein concentration were determined (as described in Example I) in culture supernatant.

The chitosanase production medium contained, for 1 000 ml, 20 g of malt extract, 4 g $KH_2PO_4$, 22 g $K_2HPO_4$, 5.6 g $(NH_4)_2SO_4$ and distilled $H_2O$. The pH was adjusted to 6.9 and the volume to 975 ml. The chitosanase production medium was autoclaved for 15 min. Before use, 25 ml of $MgSO_4$ 5% in distilled water (0.22 μm filtered sterilized) was aseptically added.

TABLE 10

Chitosanase production characterization in function of time.

| Time (h) | Chitosanase (U/ml) | Protease (U/ml) | Total proteins (μg/ml) |
|---|---|---|---|
| 24 | 0.6 | nd* | nm** |
| 48 | 4.1 | nd | nm |
| 72 | 14.9 | nd | 421.9 |
| 96 | 25.1 | 6.3 | 623.2 |

*nd: activity not detected (under detection limit)
**nm: not measure

REFERENCES

Aretz W, Koller K P, Riess G: Proteolytic enzymes from recombinant *Streptomyces lividans* TK24. FEMS Microbiol Lett 1989, 65:31-36.

Bertram R., et al. 2004. In silico and transcriptional analysis of carbohydrate systems of *Streptomyces coelicolor* A3(2). J. Bacteriol. 186:1362-1373.

DeWitt J P: Evidence for a sex factor in *Streptomyces erythraeus*. *J Bacteriol* 1985, 164:969-971.

Dubeau M-P, Broussau S, Gervais A, Masson J-Y, Brzezinski R: A palindromic DNA sequence involved in the regulation of chitosanase gene expression in actinomycetes. In *Advances in Chitin Sciences. Volume* 8. Edited by Struszczyk H, Domard A, Peter M G, Pospieszny H. Poznań: Institute of plant protection; 2005:93-100.

Dubeau M-P, Ghinet M G, Jacques P-E, Clermont N, Beaulieu C, Brzezinski R: Cytosine deaminase as negative selection marker for gene disruption and replacement in the genus *Streptomyces* and other actinobacteria. *Appl Environ Microbiol* 2009, 75:1211-1214.

Ho S N, Hunt H D, Horton R M, Pullen J K, Pease L R: Site-directed mutagenesis by overlap extension using the polymerase chain reaction. Gene 1989, 77:51-59.

Kieser T, Bibb M J, Buttner M J, Chater K F, Hopwood D A: *Practical Streptomyces genetics*. The John Innes Foundation, Norwich UK; 2000.

Lacombe-Harvey M-È, Fukamizo T, Gagnon J, Ghinet M G, Dennhart N, Letzel T, Brzezinski R: Accessory active site residues of *Streptomyces* sp. N174 chitosanase—variations on a common theme in the lysozyme superfamily. *FEBS J* 2009, 276:857-869.

Labes G, Bibb M, Wohlleben W: Isolation and characterization of a strong promoter element from the *Streptomyces ghanaensis* phage I19 using the gentamicin resistance gene (aacC1) of Tn1696 as reporter. *Microbiology* 1997, 143: 1503-1512.

Laing E., Mersinias V., Smith C. P., Hubbard S. J. 2006. Analysis of gene expression in operons of *Streptomyces coelicolor*. Genome Biol. 7:R46.

Masson J-Y, Li T, Boucher I, Beaulieu C, Brzezinski R: Factors governing an efficient chitosanase production by recombinant *Streptomyces lividans* strains carrying the cloned chs gene from *Streptomyces* N174. In *Chitin enzymology*. Edited by Muzzarelli R A A. Lyon: European Chitin Society; 1993:423-430.

Masson J-Y, Boucher I, Neugebauer W A, Ramotar D, Brzezinski R: A new chitosanase gene from a *Nocardioides* sp. is a third member of glycosyl hydrolase family 46. *Microbiology* 1995, 141:2629-2635.

Pagé N, Kluepfel D, Shareck F, Morosoli R: Effect of signal peptide alteration and replacement on export of xylanase A in *Streptomyces lividans*. *Appl Environ Microbiol* 1996, 62:109-114.

Pfaffl M. W. 2001. A new mathematical model for relative quantification in real-time-RT-PCR. Nucleic Acids Res. 29:2002-2007.

Titgemeyer F., Reizer J., Reizer A., Saier M. H., Jr 1994. Evolutionary relationships between sugar kinases and transcriptional repressors in bacteria. Microbiology 140:2349-2354.

Zitouni M, Fortin M, Thibeault J-S, Brzezinski R: A dye-labelled soluble substrate for the assay of endo-chitosanase activity. *Carbohyd Polym* 2010, 80:521-524.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A genetically modified actinobacterium cell for the production of an enzyme having chitosanase activity, said genetically modified actinobacterium cell having a disrupted open-reading frame in a csnR gene or a csnR gene ortholog and at least one exogenous nucleic acid molecule coding for the enzyme having chitosanase activity, wherein said exogenous nucleic acid molecule gene has an upstream CsnR operator comprising the consensus sequence of SEQ ID NO: 88.

2. The genetically modified actinobacterium cell of claim 1 being a *Streptomyces*.

3. The genetically modified actinobacterium cell of claim 1 being a *Streptomyces lividans*.

4. The genetically modified actinobacterium cell of claim 1, wherein the enzyme has an exo-chitosanase activity.

5. The genetically modified actinobacterium cell of claim 4, wherein the enzyme is from the glycoside hydrolase (GH) 2 family.

6. The genetically modified actinobacterium cell of claim 1, wherein the enzyme has an endo-chitosanase activity.

7. The genetically modified actinobacterium cell of claim 6, wherein the enzyme further comprises at least one of a beta-1,4-glucanase activity and/or a licheninase activity.

8. The genetically modified actinobacterium cell of claim 6, wherein the enzyme is at least from the glycoside hydrolase (GH) 5, 8 or 46 family.

9. The genetically modified actinobacterium cell of claim 1, wherein the enzyme is encoded by a nucleic acid vector.

10. The genetically modified actinobacterium cell of claim 9, wherein the nucleic acid vector is an integratable vector.

11. The genetically modified actinobacterium cell of claim 1, wherein a fragment of the csnR gene is deleted.

12. The genetically modified actinobacterium cell of claim 1, wherein an exogenous nucleic acid molecule is inserted in the open-reading frame of the csnR gene.

13. The genetically modified actinobacterium cell of claim 1, wherein a complete csnR gene is deleted.

14. A method for producing an enzyme having chitosanase activity, said method comprising (i) placing the genetically modified actinobacterium cell of claim 1 in a culture medium devoid of chitosan, chitosan fragments or chitosan derivatives and (ii) culturing the genetically modified actinobacterium cell under conditions suitable for the production of the chitosanase.

15. The method of claim 14, further comprising (iii) purifying the chitosanase from the culture medium.

16. The method of claim 14, wherein the culture medium comprises malt extract, $KH_2PO_4$, $K_2HPO_4$, $(NH_4)_2SO_4$ and $MgSO_4$.

17. A method of reducing the molecular weight of a chitosan molecule, said method comprising contacting the enzyme produced by the method of claim 14 with said chitosan molecule under conditions sufficient to allow the cleavage of said chitosan molecule by said enzyme.

18. A method of producing a low-molecular weight chitosan, said method comprising contacting the enzyme produced by the method of claim 14 with a chitosan molecule under conditions sufficient to allow the cleavage of said chitosan molecule by said enzyme into said low molecular weight chitosan.

19. A method of producing a chitosan oligosaccharide, said method comprising contacting the enzyme produced by the method of claim 14 with a chitosan molecule under conditions sufficient to allow the cleavage of said chitosan molecule by said enzyme into said chitosan oligosaccharide.

\* \* \* \* \*

SEQUENCE LISTING

```
<160> NUMBER OF SEQ ID NOS: 92

<210> SEQ ID NO 1
<211> LENGTH: 178
<212> TYPE: DNA
<213> ORGANISM: Artificial Sequence
<220> FEATURE:
<223> OTHER INFORMATION: Artificially synthesized oligonucleotide

<400> SEQUENCE: 1
atcctgacgg cccgtccgcc cagcggtacg agggcccga ccggagttcc ggtcggggcc        60
tttcgcatga ccgcgcgggc aaacatggcg cttgaccttg atgaggcggc gtgagctaca      120
atcaatatct agttaggaaa ctttcctaac tctcctcatg ggtccggaga cccgcatg       178

<210> SEQ ID NO 2
<211> LENGTH: 171
<212> TYPE: DNA
<213> ORGANISM: Artificial Sequence
<220> FEATURE:
<223> OTHER INFORMATION: Artificially synthesized oligonucleotide

<400> SEQUENCE: 2
cgggtctccg gacccatgag gagagttagg aaagtttcct aactagatat tgattgtagc        60
tcacgccgcc tcatcaaggt caagcgccat gtttgcccgc gcggtcatgc gaaaggcccc      120
gaccggaact ccggtcgggg ccctcgtacc gctgggcgga cgggccgtca g              171
```

<210> SEQ ID NO 3
<211> LENGTH: 22
<212> TYPE: DNA
<213> ORGANISM: Artificial Sequence
<220> FEATURE:
<223> OTHER INFORMATION: Artificially synthesized oligonucleotide

<400> SEQUENCE: 3
ccggagaccc gcatgccccg ga                                              22

<210> SEQ ID NO 4
<211> LENGTH: 23
<212> TYPE: DNA
<213> ORGANISM: Artificial Sequence
<220> FEATURE:
<223> OTHER INFORMATION: Artificially synthesized oligonucleotide

<400> SEQUENCE: 4
cggtgcgcca agcttgcgtt cgg                                             23

<210> SEQ ID NO 5
<211> LENGTH: 23
<212> TYPE: DNA
<213> ORGANISM: Artificial Sequence
<220> FEATURE:
<223> OTHER INFORMATION: Artificially synthesized oligonucleotide

<400> SEQUENCE: 5
gtctgcgcgg atcctgacgg ccc                                             23

<210> SEQ ID NO 6
<211> LENGTH: 23
<212> TYPE: DNA
<213> ORGANISM: Artificial Sequence
<220> FEATURE:
<223> OTHER INFORMATION: Artificially synthesized oligonucleotide

<400> SEQUENCE: 6
gtccggggca tgcgggtctc cgg                                             23

<210> SEQ ID NO 7
<211> LENGTH: 22
<212> TYPE: DNA
<213> ORGANISM: Artificial Sequence
<220> FEATURE:
<223> OTHER INFORMATION: Artificially synthesized oligonucleotide

<400> SEQUENCE: 7
acaacttcgt cgcgcacatc ca                                              22

<210> SEQ ID NO 8
<211> LENGTH: 23
<212> TYPE: DNA
<213> ORGANISM: Artificial Sequence
<220> FEATURE:
<223> OTHER INFORMATION: Artificially synthesized oligonucleotide

<400> SEQUENCE: 8
atgaggagag ttcggacagt ttc                                             23

<210> SEQ ID NO 9
<211> LENGTH: 23
<212> TYPE: DNA
<213> ORGANISM: Artificial Sequence
<220> FEATURE:
<223> OTHER INFORMATION: Artificially synthesized oligonucleotide

```
<400> SEQUENCE: 9
gaaactgtcc gaactctcct cat                                           23

<210> SEQ ID NO 10
<211> LENGTH: 22
<212> TYPE: DNA
<213> ORGANISM: Artificial Sequence
<220> FEATURE:
<223> OTHER INFORMATION: Artificially synthesized oligonucleotide

<400> SEQUENCE: 10
tgaggtcgaa gttcttggcg tt                                            22

<210> SEQ ID NO 11
<211> LENGTH: 22
<212> TYPE: DNA
<213> ORGANISM: Artificial Sequence
<220> FEATURE:
<223> OTHER INFORMATION: Artificially synthesized oligonucleotide

<400> SEQUENCE: 11
acaacttcgt cgcgcacatc ca                                            22

<210> SEQ ID NO 12
<211> LENGTH: 21
<212> TYPE: DNA
<213> ORGANISM: Artificial Sequence
<220> FEATURE:
<223> OTHER INFORMATION: Artificially synthesized oligonucleotide

<400> SEQUENCE: 12
ttaatacgac tcactatagg g                                             21

<210> SEQ ID NO 13
<211> LENGTH: 19
<212> TYPE: DNA
<213> ORGANISM: Artificial Sequence
<220> FEATURE:
<223> OTHER INFORMATION: Artificially synthesized oligonucleotide

<400> SEQUENCE: 13
tggggtgctt gagacgcat                                                19

<210> SEQ ID NO 14
<211> LENGTH: 34
<212> TYPE: DNA
<213> ORGANISM: Streptomyces lividans

<400> SEQUENCE: 14
aggagagtta ggaaagtttc ctaactagat tgaa                               34

<210> SEQ ID NO 15
<211> LENGTH: 63
<212> TYPE: DNA
<213> ORGANISM: Streptomyces lividans

<400> SEQUENCE: 15
cagggccttg cgcggtggtg ggcgtgaacg cttcaatcta gttaggaaac tttcctaact   60
ctc                                                                 63

<210> SEQ ID NO 16
<211> LENGTH: 63
<212> TYPE: DNA
<213> ORGANISM: Artificial Sequence
<220> FEATURE:
```

<223> OTHER INFORMATION: Mutated promoter from S. lividans with promoter
      from S. ghanaesis phage I19

<400> SEQUENCE: 16
ttgaccttga tgaggcggcg tgagctacaa tcaatatcta gttaggaaac tttcctaact    60
ctc                                                                 63

<210> SEQ ID NO 17
<211> LENGTH: 63
<212> TYPE: DNA
<213> ORGANISM: Streptomyces lividans

<400> SEQUENCE: 17
ttgaccttga tgaggcggcg tgagctacaa tcaatatcta gttaggaaac tttcctaact    60
ctc                                                                 63

<210> SEQ ID NO 18
<211> LENGTH: 31
<212> TYPE: DNA
<213> ORGANISM: Streptomyces sp.

<400> SEQUENCE: 18
tgaatcggtt aggaaagttt cctaactctc t                                   31

<210> SEQ ID NO 19
<211> LENGTH: 31
<212> TYPE: DNA
<213> ORGANISM: Streptomyces coelicolor

<400> SEQUENCE: 19
tgaatcggtt aggaaagttt cctaactctc t                                   31

<210> SEQ ID NO 20
<211> LENGTH: 31
<212> TYPE: DNA
<213> ORGANISM: Streptomyces lividans

<400> SEQUENCE: 20
ttcttctggt aggaaacttt cctatcagtg c                                   31

<210> SEQ ID NO 21
<211> LENGTH: 31
<212> TYPE: DNA
<213> ORGANISM: Streptomyces avermitilis

<400> SEQUENCE: 21
gaactctggt aggaaacttt cctaacagta c                                   31

<210> SEQ ID NO 22
<211> LENGTH: 31
<212> TYPE: DNA
<213> ORGANISM: Streptomyces avermitilis

<400> SEQUENCE: 22
caacatggta aggaaacttt cctaacagaa g                                   31

<210> SEQ ID NO 23
<211> LENGTH: 31
<212> TYPE: DNA
<213> ORGANISM: Streptomyces scabies

<400> SEQUENCE: 23
cctttctgtt aggaaagttt cctactagtt c                                   31

```
<210> SEQ ID NO 24
<211> LENGTH: 31
<212> TYPE: DNA
<213> ORGANISM: Streptomyces griseus

<400> SEQUENCE: 24
gttaatagac aggaaagttt cccaacactg t                               31

<210> SEQ ID NO 25
<211> LENGTH: 29
<212> TYPE: DNA
<213> ORGANISM: Artificial Sequence
<220> FEATURE:
<223> OTHER INFORMATION: Artificial promoter consensus sequence
<220> FEATURE:
<221> NAME/KEY: misc_feature
<222> LOCATION: (1)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t

<400> SEQUENCE: 25
nnnnncngtt aggaaacttt cctaacagt                                  29

<210> SEQ ID NO 26
<211> LENGTH: 24
<212> TYPE: DNA
<213> ORGANISM: Artificial Sequence
<220> FEATURE:
<223> OTHER INFORMATION: Artificially synthesized oligonucleotide

<400> SEQUENCE: 26
gcggtcgaat tccaggtgtg gaca                                       24

<210> SEQ ID NO 27
<211> LENGTH: 22
<212> TYPE: DNA
<213> ORGANISM: Artificial Sequence
<220> FEATURE:
<223> OTHER INFORMATION: Artificially synthesized oligonucleotide

<400> SEQUENCE: 27
attccgggcc tcgagaagct cc                                         22

<210> SEQ ID NO 28
<211> LENGTH: 17
<212> TYPE: DNA
<213> ORGANISM: Artificial Sequence
<220> FEATURE:
<223> OTHER INFORMATION: Artificially synthesized oligonucleotide

<400> SEQUENCE: 28
cctgccatgc gtgtcca                                               17

<210> SEQ ID NO 29
<211> LENGTH: 17
<212> TYPE: DNA
<213> ORGANISM: Artificial Sequence
<220> FEATURE:
<223> OTHER INFORMATION: Artificially synthesized oligonucleotide

<400> SEQUENCE: 29
cggaaggggt gcctcac                                               17
```

```
<210> SEQ ID NO 30
<211> LENGTH: 22
<212> TYPE: DNA
<213> ORGANISM: Artificial Sequence
<220> FEATURE:
<223> OTHER INFORMATION: Artificially synthesized oligonucleotide

<400> SEQUENCE: 30
acaacttcgt cgcgcacatc ca                                              22

<210> SEQ ID NO 31
<211> LENGTH: 23
<212> TYPE: DNA
<213> ORGANISM: Artificial Sequence
<220> FEATURE:
<223> OTHER INFORMATION: Artificially synthesized oligonucleotide

<400> SEQUENCE: 31
ggagcagccg gatccctgac gga                                             23

<210> SEQ ID NO 32
<211> LENGTH: 23
<212> TYPE: DNA
<213> ORGANISM: Artificial Sequence
<220> FEATURE:
<223> OTHER INFORMATION: Artificially synthesized oligonucleotide

<400> SEQUENCE: 32
aggggtgccg catgcaatct cca                                             23

<210> SEQ ID NO 33
<211> LENGTH: 23
<212> TYPE: DNA
<213> ORGANISM: Artificial Sequence
<220> FEATURE:
<223> OTHER INFORMATION: Artificially synthesized oligonucleotide

<400> SEQUENCE: 33
gcaccagcaa ggatccccgc ccg                                             23

<210> SEQ ID NO 34
<211> LENGTH: 23
<212> TYPE: DNA
<213> ORGANISM: Artificial Sequence
<220> FEATURE:
<223> OTHER INFORMATION: Artificially synthesized oligonucleotide

<400> SEQUENCE: 34
tgcgtgtccg catgcgcctc tcg                                             23

<210> SEQ ID NO 35
<211> LENGTH: 22
<212> TYPE: DNA
<213> ORGANISM: Artificial Sequence
<220> FEATURE:
<223> OTHER INFORMATION: Artificially synthesized oligonucleotide

<400> SEQUENCE: 35
aatacgacac cagatggacg gc                                              22

<210> SEQ ID NO 36
<211> LENGTH: 23
<212> TYPE: DNA
<213> ORGANISM: Artificial Sequence
<220> FEATURE:
<223> OTHER INFORMATION: Artificially synthesized oligonucleotide

<400> SEQUENCE: 36
```
ccgggcactg atcggacagt ttc                                              23

<210> SEQ ID NO 37
<211> LENGTH: 23
<212> TYPE: DNA
<213> ORGANISM: Artificial Sequence
<220> FEATURE:
<223> OTHER INFORMATION: Artificially synthesized oligonucleotide

<400> SEQUENCE: 37
gaaactgtcc gatcagtgcc cgg                                              23

<210> SEQ ID NO 38
<211> LENGTH: 23
<212> TYPE: DNA
<213> ORGANISM: Artificial Sequence
<220> FEATURE:
<223> OTHER INFORMATION: Artificially synthesized oligonucleotide

<400> SEQUENCE: 38
ttgtcctcca ccttccagtc ctt                                              23

<210> SEQ ID NO 39
<211> LENGTH: 21
<212> TYPE: DNA
<213> ORGANISM: Artificial Sequence
<220> FEATURE:
<223> OTHER INFORMATION: Artificially synthesized oligonucleotide

<400> SEQUENCE: 39
tccgccgtct agaaccagca a                                                21

<210> SEQ ID NO 40
<211> LENGTH: 22
<212> TYPE: DNA
<213> ORGANISM: Artificial Sequence
<220> FEATURE:
<223> OTHER INFORMATION: Artificially synthesized oligonucleotide

<400> SEQUENCE: 40
cgagggccgg aattctggat at                                               22

<210> SEQ ID NO 41
<211> LENGTH: 30
<212> TYPE: DNA
<213> ORGANISM: Artificial Sequence
<220> FEATURE:
<223> OTHER INFORMATION: Artificially synthesized oligonucleotide

<400> SEQUENCE: 41
ctccagccaa caggaaactt tcctaacaga                                       30

<210> SEQ ID NO 42
<211> LENGTH: 30
<212> TYPE: DNA
<213> ORGANISM: Artificial Sequence
<220> FEATURE:
<223> OTHER INFORMATION: Artificially synthesized oligonucleotide

<400> SEQUENCE: 42
cctcttctgg taggaaactt tcctatcagt                                       30

<210> SEQ ID NO 43
<211> LENGTH: 30
<212> TYPE: DNA
<213> ORGANISM: Artificial Sequence

```
<220> FEATURE:
<223> OTHER INFORMATION: Artificially synthesized oligonucleotide

<400> SEQUENCE: 43
cctcttctgg taggaaactg tcctatcagt                                30

<210> SEQ ID NO 44
<211> LENGTH: 30
<212> TYPE: DNA
<213> ORGANISM: Artificial Sequence
<220> FEATURE:
<223> OTHER INFORMATION: Artificially synthesized oligonucleotide

<400> SEQUENCE: 44
cctcttctgg taggaaactt tccgatcagt                                30

<210> SEQ ID NO 45
<211> LENGTH: 30
<212> TYPE: DNA
<213> ORGANISM: Artificial Sequence
<220> FEATURE:
<223> OTHER INFORMATION: Artificially synthesized oligonucleotide

<400> SEQUENCE: 45
cctcttctgg taggaaactg tccgatcagt                                30

<210> SEQ ID NO 46
<211> LENGTH: 22
<212> TYPE: DNA
<213> ORGANISM: Artificial Sequence
<220> FEATURE:
<223> OTHER INFORMATION: Artificially synthesized oligonucleotide

<400> SEQUENCE: 46
accggtacat cgaggacatc gg                                        22

<210> SEQ ID NO 47
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 47
agatagggcg cgaggacgtt                                           20

<210> SEQ ID NO 48
<211> LENGTH: 24
<212> TYPE: DNA
<213> ORGANISM: Artificial Sequence
<220> FEATURE:
<223> OTHER INFORMATION: Artificially synthesized oligonucleotide

<400> SEQUENCE: 48
ggtcgagtac gagaacgacg tgaa                                      24

<210> SEQ ID NO 49
<211> LENGTH: 22
<212> TYPE: DNA
<213> ORGANISM: Artificial Sequence
<220> FEATURE:
<223> OTHER INFORMATION: Artificially synthesized oligonucleotide

<400> SEQUENCE: 49
tggttccaca gcaggacgaa gt                                        22
```

```
<210> SEQ ID NO 50
<211> LENGTH: 22
<212> TYPE: DNA
<213> ORGANISM: Artificial Sequence
<220> FEATURE:
<223> OTHER INFORMATION: Artificially synthesized oligonucleotide

<400> SEQUENCE: 50
gaactaccac ggctacgaga cc                                          22

<210> SEQ ID NO 51
<211> LENGTH: 24
<212> TYPE: DNA
<213> ORGANISM: Artificial Sequence
<220> FEATURE:
<223> OTHER INFORMATION: Artificially synthesized oligonucleotide

<400> SEQUENCE: 51
tgttgcggta cttctccagc ttct                                        24

<210> SEQ ID NO 52
<211> LENGTH: 24
<212> TYPE: DNA
<213> ORGANISM: Artificial Sequence
<220> FEATURE:
<223> OTHER INFORMATION: Artificially synthesized oligonucleotide

<400> SEQUENCE: 52
cctcctacta cctgcgctac tact                                        24

<210> SEQ ID NO 53
<211> LENGTH: 23
<212> TYPE: DNA
<213> ORGANISM: Artificial Sequence
<220> FEATURE:
<223> OTHER INFORMATION: Artificially synthesized oligonucleotide

<400> SEQUENCE: 53
atctgcagca gttgccgttc cat                                         23

<210> SEQ ID NO 54
<211> LENGTH: 22
<212> TYPE: DNA
<213> ORGANISM: Artificial Sequence
<220> FEATURE:
<223> OTHER INFORMATION: Artificially synthesized oligonucleotide

<400> SEQUENCE: 54
gccgagaact cgaccacgaa gt                                          22

<210> SEQ ID NO 55
<211> LENGTH: 21
<212> TYPE: DNA
<213> ORGANISM: Artificial Sequence
<220> FEATURE:
<223> OTHER INFORMATION: Artificially synthesized oligonucleotide

<400> SEQUENCE: 55
tgtagcgctc gaccagcatg a                                           21

<210> SEQ ID NO 56
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 56
```
accaccatcg cgaagctcaa                    20

<210> SEQ ID NO 57
<211> LENGTH: 24
<212> TYPE: DNA
<213> ORGANISM: Artificial Sequence
<220> FEATURE:
<223> OTHER INFORMATION: Artificially synthesized oligonucleotide

<400> SEQUENCE: 57
gcatctcctt ctgcatcttc tcgt               24

<210> SEQ ID NO 58
<211> LENGTH: 25
<212> TYPE: DNA
<213> ORGANISM: Artificial Sequence
<220> FEATURE:
<223> OTHER INFORMATION: Artificially synthesized oligonucleotide

<400> SEQUENCE: 58
gcgacgaccg caagaccaag ctgat              25

<210> SEQ ID NO 59
<211> LENGTH: 25
<212> TYPE: DNA
<213> ORGANISM: Artificial Sequence
<220> FEATURE:
<223> OTHER INFORMATION: Artificially synthesized oligonucleotide

<400> SEQUENCE: 59
tgacgacgat gtcctcctcg gcgat              25

<210> SEQ ID NO 60
<211> LENGTH: 25
<212> TYPE: DNA
<213> ORGANISM: Artificial Sequence
<220> FEATURE:
<223> OTHER INFORMATION: Artificially synthesized oligonucleotide

<400> SEQUENCE: 60
tctgggccga tactgacgct gagga              25

<210> SEQ ID NO 61
<211> LENGTH: 25
<212> TYPE: DNA
<213> ORGANISM: Artificial Sequence
<220> FEATURE:
<223> OTHER INFORMATION: Artificially synthesized oligonucleotide

<400> SEQUENCE: 61
atgttgccca cacctagtgc ccacc               25

<210> SEQ ID NO 62
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 62
ttccaggtgc cgtggtggta                    20

<210> SEQ ID NO 63
<211> LENGTH: 20
<212> TYPE: DNA
<213> ORGANISM: Artificial Sequence

```
<220> FEATURE:
<223> OTHER INFORMATION: Artificially synthesized oligonucleotide

<400> SEQUENCE: 63
agccagtcga tccagcccat                                                     20

<210> SEQ ID NO 64
<211> LENGTH: 21
<212> TYPE: DNA
<213> ORGANISM: Artificial Sequence
<220> FEATURE:
<223> OTHER INFORMATION: Artificially synthesized oligonucleotide

<400> SEQUENCE: 64
caccagcttc agcagcatcc g                                                   21

<210> SEQ ID NO 65
<211> LENGTH: 21
<212> TYPE: DNA
<213> ORGANISM: Artificial Sequence
<220> FEATURE:
<223> OTHER INFORMATION: Artificially synthesized oligonucleotide

<400> SEQUENCE: 65
agccgatgtg gtagctgtcc c                                                   21

<210> SEQ ID NO 66
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 66
gccatgaaac gtgccgctct                                                     20

<210> SEQ ID NO 67
<211> LENGTH: 21
<212> TYPE: DNA
<213> ORGANISM: Artificial Sequence
<220> FEATURE:
<223> OTHER INFORMATION: Artificially synthesized oligonucleotide

<400> SEQUENCE: 67
gccagtccag ggtggagttc t                                                   21

<210> SEQ ID NO 68
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 68
aatgccgaga ccctgccgta                                                     20

<210> SEQ ID NO 69
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 69
acgtggttct cgatgggcga                                                     20
```

```
<210> SEQ ID NO 70
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 70
ttccaccagt ccgacggcaa                                              20

<210> SEQ ID NO 71
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 71
atgggcgaga cctgcgagtt                                              20

<210> SEQ ID NO 72
<211> LENGTH: 22
<212> TYPE: DNA
<213> ORGANISM: Artificial Sequence
<220> FEATURE:
<223> OTHER INFORMATION: Artificially synthesized oligonucleotide

<400> SEQUENCE: 72
gcaggaagtc aacgagccct tc                                           22

<210> SEQ ID NO 73
<211> LENGTH: 21
<212> TYPE: DNA
<213> ORGANISM: Artificial Sequence
<220> FEATURE:
<223> OTHER INFORMATION: Artificially synthesized oligonucleotide

<400> SEQUENCE: 73
cttgctgtac tgcggggcct t                                            21

<210> SEQ ID NO 74
<211> LENGTH: 30
<212> TYPE: DNA
<213> ORGANISM: Kitasatosporia sp.

<400> SEQUENCE: 74
tcaatctagt taggaaactt tcctaactct                                   30

<210> SEQ ID NO 75
<211> LENGTH: 30
<212> TYPE: DNA
<213> ORGANISM: Streptomyces sp.

<400> SEQUENCE: 75
ttgaatcggt taggaaagtt tcctaactct                                   30

<210> SEQ ID NO 76
<211> LENGTH: 30
<212> TYPE: DNA
<213> ORGANISM: Streptomyces coelicolor

<400> SEQUENCE: 76
cctcttctgg taggaaactt tcctatcagt                                   30

<210> SEQ ID NO 77
<211> LENGTH: 30
```

```
<212> TYPE: DNA
<213> ORGANISM: Streptomyces lividans

<400> SEQUENCE: 77
cttcttctgg taggaaactt tcctatcagt                                    30

<210> SEQ ID NO 78
<211> LENGTH: 30
<212> TYPE: DNA
<213> ORGANISM: Streptomyces avermitilis

<400> SEQUENCE: 78
cgaactctgg taggaaactt tcctaacagt                                    30

<210> SEQ ID NO 79
<211> LENGTH: 30
<212> TYPE: DNA
<213> ORGANISM: Streptomyces avermitilis

<400> SEQUENCE: 79
gcaacatggt aaggaaactt tcctaacaga                                    30

<210> SEQ ID NO 80
<211> LENGTH: 30
<212> TYPE: DNA
<213> ORGANISM: Streptomyces scabies

<400> SEQUENCE: 80
ccctttctgt taggaaagtt tcctactagt                                    30

<210> SEQ ID NO 81
<211> LENGTH: 30
<212> TYPE: DNA
<213> ORGANISM: Streptomyces griseus

<400> SEQUENCE: 81
tgttaataga caggaaagtt tcccaacact                                    30

<210> SEQ ID NO 82
<211> LENGTH: 30
<212> TYPE: DNA
<213> ORGANISM: Streptomyces avermitilis

<400> SEQUENCE: 82
tgaatccagt tagtaaagtt tcctaacttg                                    30

<210> SEQ ID NO 83
<211> LENGTH: 30
<212> TYPE: DNA
<213> ORGANISM: Streptomyces coelicolor

<400> SEQUENCE: 83
ctccagccaa caggaaactt tcctaacaga                                    30

<210> SEQ ID NO 84
<211> LENGTH: 30
<212> TYPE: DNA
<213> ORGANISM: Streptomyces lividans

<400> SEQUENCE: 84
ctccagccaa caggaaactt tcctaacaga                                    30

<210> SEQ ID NO 85
<211> LENGTH: 30
```

```
<212> TYPE: DNA
<213> ORGANISM: Streptomyces avermitilis

<400> SEQUENCE: 85
ctcccaccaa taggaaactt tcctaacaat                                        30

<210> SEQ ID NO 86
<211> LENGTH: 30
<212> TYPE: DNA
<213> ORGANISM: Streptomyces scabies

<400> SEQUENCE: 86
tggcatccga caggaaagtt tcctaacagt                                        30

<210> SEQ ID NO 87
<211> LENGTH: 30
<212> TYPE: DNA
<213> ORGANISM: Streptomyces griseus

<400> SEQUENCE: 87
ctcaaccgaa taggaaactt tcctaacaga                                        30

<210> SEQ ID NO 88
<211> LENGTH: 27
<212> TYPE: DNA
<213> ORGANISM: Artificial Sequence
<220> FEATURE:
<223> OTHER INFORMATION: Artificial consensus sequence
<220> FEATURE:
<221> NAME/KEY: misc_feature
<222> LOCATION: (1)..(3)
<223> OTHER INFORMATION: m is a or c
<220> FEATURE:
<221> NAME/KEY: misc_feature
<222> LOCATION: (4)..(4)
<223> OTHER INFORMATION: y is c or t
<220> FEATURE:
<221> NAME/KEY: misc_feature
<222> LOCATION: (5)..(5)
<223> OTHER INFORMATION: b is c, g, or t
<220> FEATURE:
<221> NAME/KEY: misc_feature
<222> LOCATION: (6)..(26)
<223> OTHER INFORMATION: r is a or g
<220> FEATURE:
<221> NAME/KEY: misc_feature
<222> LOCATION: (7)..(27)
<223> OTHER INFORMATION: w is a or t
<220> FEATURE:
<221> NAME/KEY: misc_feature
<222> LOCATION: (15)..(15)
<223> OTHER INFORMATION: n is c or g

<400> SEQUENCE: 88
mmmybrwtag gaaastttcc taacwrw                                           27

<210> SEQ ID NO 89
<211> LENGTH: 107
<212> TYPE: DNA
<213> ORGANISM: Streptomyces lividans

<400> SEQUENCE: 89
cagttcgtgc acgacgggtg cccggcacgc ccctcttctg gtaggaaact ttcctatcag       60
```

```
                                    -continued
tgcccggcac tcccctcccc cactccccca cacctggaga ttccgtg               107

<210> SEQ ID NO 90
<211> LENGTH: 150
<212> TYPE: DNA
<213> ORGANISM: Artificial Sequence
<220> FEATURE:
<223> OTHER INFORMATION: Artificially synthesized oligonucleotide

<400> SEQUENCE: 90
cttgacggct ccttgcgggc gggcctacgt tctccagcca acaggaaact ttcctaacag    60
acgcactcgg gcgtcccgcc ggaacgtgtc ccgtgatccg cgcggtggac ttcccccacc   120
accccctgaa aagctgagcg gtcgagaggc                                    150

<210> SEQ ID NO 91
<211> LENGTH: 180
<212> TYPE: DNA
<213> ORGANISM: Streptomyces lividans

<400> SEQUENCE: 91
gagagtgcgc tcgcgaccac ccgcgacgag gtcttcgaca cctcgcgctg accccgcgc    60 caccccgccc cgcgccaccc cgccccgcgc caccccgccc cgcgccaccc actcgcccca   120
cccacctgtc ccccgccctg ccctgggag cttcgccatg cccggaatat ccagaaaagc   180

<210> SEQ ID NO 92
<211> LENGTH: 148
<212> TYPE: DNA
<213> ORGANISM: Streptomyces coelicolor

<400> SEQUENCE: 92
gagagtgcgc tcgcgaccac ccgcgacgag gtcttcgaca cctcgcgctg accccgcgcc    60
accccgcccc gcgccaccca ctcgccccac ccacctgtcc ccgccctgcc cctgggagct   120
tcgccatgcc cggaatatcc agaaaagc                                     148
```